United States Patent
Diaz et al.

(10) Patent No.: US 7,246,522 B1
(45) Date of Patent: Jul. 24, 2007

(54) METHODS AND APPARATUS FOR MULTI-PARAMETER ACOUSTIC SIGNATURE INSPECTION

(75) Inventors: Aaron A. Diaz, Richland, WA (US); Todd J. Samuel, Pasco, WA (US); Juan D. Valencia, Kennewick, WA (US); Kevin L. Gervais, Richland, WA (US); Brian J. Tucker, Pasco, WA (US); Leslie J. Kirihara, Richland, WA (US); James R. Skorpik, Kennewick, WA (US); Larry D. Reid, Benton City, WA (US); John T. Munley, Benton City, WA (US); Richard A. Pappas, Richland, WA (US); Bob W. Wright, West Richland, WA (US); Paul D. Panetta, Richland, WA (US); Jason S. Thompson, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 11/361,266

(22) Filed: Feb. 24, 2006

(51) Int. Cl.
*G01N 29/18* (2006.01)

(52) U.S. Cl. ............................. 73/597; 73/64.53; 73/52

(58) Field of Classification Search .......... 73/596–600, 73/632, 644, 61.49, 61.75, 61.79, 64.53, 73/52, 602
See application file for complete search history.

(56) References Cited

U.S. PATENT DOCUMENTS

| 3,942,381 | A | * | 3/1976 | Brown et al. ................. 73/703 |
| 5,767,407 | A | * | 6/1998 | Sinha .......................... 73/579 |
| 6,247,353 | B1 | * | 6/2001 | Battenberg et al. ...... 73/40.5 A |
| 2004/0035208 | A1 | * | 2/2004 | Diaz et al. .................... 73/597 |

OTHER PUBLICATIONS

Brian J. Tucker, et al., (abstract paper) Advanced ultrasonic measurement methnodology for non-invasive interrogation and identification of fluids in sealed containers.

Brian J. Tucker, et al, (Presentation) Prototype instrument for noninvasive ultrasonic inspection and identification of fluids in sealed containers.

* cited by examiner

*Primary Examiner*—Helen Kwok
(74) *Attorney, Agent, or Firm*—James D. Matheson

(57) ABSTRACT

A multiparameter acoustic signature inspection device and method are described for non-invasive inspection of containers. Dual acoustic signatures discriminate between various fluids and materials for identification of the same.

38 Claims, 18 Drawing Sheets

METHODS AND APPARATUS FOR MULTI-PARAMETER ACOUSTIC SIGNATURE INSPECTION

This invention was made with Government support under Contract DE-AC05-76RL01830 awarded by the U.S. Department of Energy. The Government has certain rights in the invention.

FIELD OF THE INVENTION

The invention is a method and apparatus for multiparameter acoustic signature inspection that utilizes non-intrusive/non-invasive for identification of materials and/or fluids.

BACKGROUND OF THE INVENTION

Numerous industries find it desirable to ascertain contents of containers, or to identify materials and fluids. Domestic and international applications exist in, for example, law enforcement, border control, transportation, and shipping. Internationally, ensuring treaty compliance, border control, training, and deterring illicit drug smuggling are significant applications. Other applications include efforts to collect taxes and tariffs, to effectively maintain inventories, and to monitor process flows. Further, material quality and process control are central to achieving high standards of product performance and safety in such industries as food processing and chemical inventory management. Government agencies and homeland security organizations also need ways to cope with increasing investigations involving hazardous chemical, and biological materials, including warfare agents. Due to the large number of containers being shipped both domestically and internationally, there is a need for fast and effective ways for conducting non-intrusive inspection of containers. Such inspections need to quickly identify materials and fluids within the containers and also ascertain presence of objects not expected to be in a container, including, e.g., smuggled contraband. Current systems rely heavily on expensive and time-consuming direct sampling as well as laboratory analyses.

Accordingly, there remains a need for methods and devices providing rapid and reliable inspection data for decision-making purposes for a wide diversity of materials and fluids.

SUMMARY OF THE INVENTION

In one aspect, the invention is an inspection apparatus providing multiparameter acoustic inspection and identification, comprising: at least two transducers operably disposed for inspection of a container, a material, or a fluid, wherein at least one of the at least two transducers transmits an acoustic excitation pulse(s) or waveform(s) through the container, material, or fluid for inspection of same and one or more of the at least two transducers receives the pulse(s) or waveform(s) transmitted through, and/or reflected in, the container, material or fluid; coupling means operably disposed for coupling the transducers to the container, the material, or the fluid whereby the pulse(s) or waveform(s) have sufficiently high throughput energy through the material, container, or fluid providing for analysis of same; path length measuring means operably disposed for measuring acoustic path length of the pulse(s) or waveform(s); temperature measuring means operably disposed for measuring temperature of the material, container, or fluid; circuit means operably disposed to the transducers for conditioning of the pulse(s) or waveform(s) transmitted and/or received through the container, material, or fluid; computing means electrically coupled to the circuit means providing for at least an analysis of the pulse(s) or waveform(s) conditioned by the circuit means; and, wherein analysis of the pulse(s) or waveform(s) or a portion thereof as a function of temperature yields at least a first acoustic discrimination signature and/or a second acoustic discrimination signature for identifying the material and/or the fluid being inspected.

In another aspect, the invention is a method for multiparameter acoustic inspection and identification, comprising the steps: providing an inspection apparatus comprising: at least two transducers operably disposed for inspection of a container, a material, or a fluid, at least one of the at least two transducers transmits an acoustic excitation pulse(s) or waveform(s) through the container, material, or fluid for inspection of same and one or more of the at least two transducers receives the pulse(s) or waveform(s) transmitted through, and/or reflected in, the container, material or fluid; coupling means operably disposed for coupling the transducers to the container, the material, or the fluid whereby the pulse(s) or waveform(s) have sufficiently high throughput energy through the material, container, or fluid providing for analysis of same; path length measuring means operably disposed for measuring acoustic path length of the pulse(s) or waveform(s); temperature measuring means operably disposed for measuring temperature of the material, container, or fluid; circuit means operably disposed to the transducers for conditioning of the pulse(s) or waveform(s) transmitted and/or received through the container, material, or fluid; computing means electrically coupled to the circuit means providing for at least an analysis of the pulse(s) or waveform(s) conditioned by the circuit means; and, selecting a location for transmitting the excitation pulse or waveform through the container, the material, and/or the fluid to at least the second transducer in a receiving location; transmitting the excitation pulse or waveform into the container, material, and/or fluid being inspected; receiving the excitation pulse or waveform and any reflected pulse(s) or waveform(s) through the container, material, and/or fluid; wherein analysis of the pulse(s) or waveform(s) or a portion thereof as a function of temperature yields at least a first acoustic discrimination signature and/or a second acoustic discrimination signature for identifying the material and/or the fluid being inspected.

In one embodiment, the transducers are configured for contacting opposing surfaces of a container or a material for inspection of same.

In another embodiment, at least two transducers are in vertical and horizontal alignment to each other.

In another embodiment, transducers have operational frequencies selected in the range from about 1 MHz to about 5 MHz.

In another embodiment, frequency of an excitation pulse or waveform is selected in the range from about 0 MHz to about 2 MHz, or from about 0 to about 10 MHz for a 1 MHz and 5 MHz transducer, respectively.

In another embodiment, a transducer has a pulsing frequency of 1 MHz or 5 MHz.

In another embodiment, an excitation pulse or waveform is a wide-band, frequency-modulated, amplitude-modulated excitation pulse or waveform ("chirp").

In another embodiment, the gain of an excitation pulse is automatically controlled maximizing signal amplitude through a container, a material, and/or a fluid.

In another embodiment, an excitation pulse or waveform is encoded.

In another embodiment, encoding of the excitation pulse or waveform comprises a frequency pattern.

In another embodiment, encoding comprises pulse compression of an excitation waveform whereby frequency and amplitude information in the received pulse(s) or waveform(s) permit cross-correlation of same.

In another embodiment, encoding of the excitation pulse or waveform includes pulse compression that retains frequency and amplitude information in the received waveforms permitting deconvolution and cross-correlation of received pulses or waveforms.

In another embodiment, an excitation pulse or waveform includes a linear frequency sweep with 60% of the pulse or waveform at full amplitude and a bandwidth selected in the range from about 0.2 MHz to about 1.2 MHz or greater.

In another embodiment, an excitation pulse or waveform is transmitted by a first transducer through a container, a material, or a fluid being inspected and received by one or more transducers in one or more of pitch-catch or pulse-echo modes.

In another embodiment, pulse-echo and pitch-catch (through-transmission) inspection modalities are employed to identify materials or fluids in a container.

In another embodiment, a first of at least two transducers is configured for receiving all 2·n (even) echo pulse(s) (where n=1, 2, 3 . . . ) and a second of at least two transducers is configured for receiving an excitation pulse or waveform through a container, material, or fluid and all 1·n (odd) echo pulse(s) (where n=3, 5, 7 . . . ).

In another embodiment, analysis of received pulse(s) or waveform(s) involves deconvolution by cross-correlation of same with an excitation or transmission pulse or waveform for determining acoustic wave speed as a first acoustic discrimination value and relative attenuation coefficient as a second discrimination value for identifying a material or a fluid being inspected.

In another embodiment, analysis of received pulse(s) or waveform(s) involves sampling a gated portion from a cross correlation of the pulse(s) or waveform(s) with an excitation pulse or waveform.

In another embodiment, analysis of received pulse(s) or waveform(s) involves deconvolution and a fast Fourier transform of gated portions selected from a cross correlation of the pulse(s) or waveform(s) with an excitation pulse or waveform.

In another embodiment, analysis of received pulse(s) or waveform(s) includes cross-correlation of the received echo pulse(s) with an excitation pulse or waveform that yields time-of-flight data permitting determination of acoustic wave speed as a first acoustic discrimination value and relative attenuation coefficient as a second discrimination value for identifying a material or a fluid.

In another embodiment, first and second acoustic discrimination values are acoustic wave speed and relative acoustic attenuation, respectively.

In another embodiment, at least one of at least two transducers is a transmitting transducer.

In another embodiment, reflected pulse(s) or waveform(s) through a container, material, or fluid are received by one or more transducers in receive mode.

In another embodiment, the invention includes a frame or other support means permitting extension and retraction of transducers along a horizontal axis of varying distance providing for attachment of the transducers to opposing sides of a container, or a material for inspection of same.

In another embodiment, temperature measuring means is an infra-red laser pyrometer connected to each of at least two transducers for measuring temperature.

In another embodiment, coupling means is a dry coupling means that does not require a wetting agent for contacting a container being inspected.

In another embodiment, dry coupling means is Aqualene®.

In another embodiment, coupling means has an acoustic impedance selected in the range from about 1.0 MRayls to about 3.0 MRayls.

In another embodiment, dry coupling means comprises at least one of solid water, neoprene, butyl rubber, polyurethane, RTV, silicone rubber, Ecothane®, Pellathane®, or combinations thereof.

In another embodiment, dry coupling means has an acoustic impedance no greater than $2.5$ gm cm$^{-2}$ sec$^{-1}$×$10^5$, and a longitudinal acoustic wave speed between about 0.06 to about 0.065 inches per microsecond and a density between about 1.2 to about 1.5 gm cm$^{-3}$.

In another embodiment, a coupling means for acoustically coupling transducers has an acoustic impedance substantially matching that of a container, material, or fluid being inspected.

In another embodiment, a computing means comprises a user interface for setting and/or controlling at least one of amplitude, frequency, pulse width, digitizing rate, or combinations thereof by an operator.

In another embodiment, one or more carousels holding one or more transducers mounts to a support frame permitting rotation about an axis for selection of transducers.

In another embodiment, circuit means includes a multiplexer having at least one relay and one or more Power MOSFETS for rapid switching between, and selection of, inspection modes for operation.

In another embodiment, materials and fluids in a container are identified using values for acoustic wave speed and relative attenuation coefficients determined from time-of-flight as a function of temperature.

In another embodiment, an excitation pulse is transmitted ("pitched") by a first of at least two transducers through a container, material, or fluid being inspected and received (in "pitch-catch" mode) by at least a second of at least two transducers.

In another embodiment, said first and second acoustic discrimination values are temperature compensated acoustic discrimination values.

In another embodiment, conditioning of pulse(s) or waveform(s) includes a member selected from the group consisting of amplifying, biasing, converting, demodulating, deconvoluting, rectifying, integrating, transforming, or the like, or combinations thereof.

In another embodiment, analysis of pulse(s) or waveform(s) includes correction for degree of curvature of a surface of a container or material.

In another embodiment, analysis of pulse(s) or waveform(s) includes correction for thickness of a container wall and/or composition of a container wall.

In another embodiment, acoustic wave speed and relative acoustic attenuation coefficient values include corrections for container composition selected from the group consisting of metal, plastic, ceramic, glass, or combinations thereof.

In another embodiment, thickness of a container is ascertained in conjunction with acoustic echoes and time-of-flight measurements.

In another embodiment, a computer means is a tablet PC interfaced to circuit means in conjunction with a compact flash card insert.

In another embodiment, computing means is deployable at a distance from the inspection apparatus.

In another embodiment, computing means is further configured to return and display operation parameters, inspection measurements, calculated parameters, and the like.

In another embodiment, sampling of pulse(s) or waveform(s) by a computing means is done at a frequency of 20 MHz or 100 MHz for a 1 MHz transducer and a 5 MHz transducer, respectively.

In another embodiment, path length and/or distance measuring means is an automated device selected from encoder, caliper, micrometer, laser, acoustic camera, or the like that provides a digital output useful in conjunction a computing means.

In another embodiment, a battery or battery pack system provides portability and permits field deployment.

In another embodiment, computer means is selected from laptop, mainframe, desktop, Personal Digital Assistant (PDA), tablet PC, dumb terminal, handheld computer, portable computer, or the like, or combinations thereof.

DETAILED DESCRIPTION

Figure 1A:
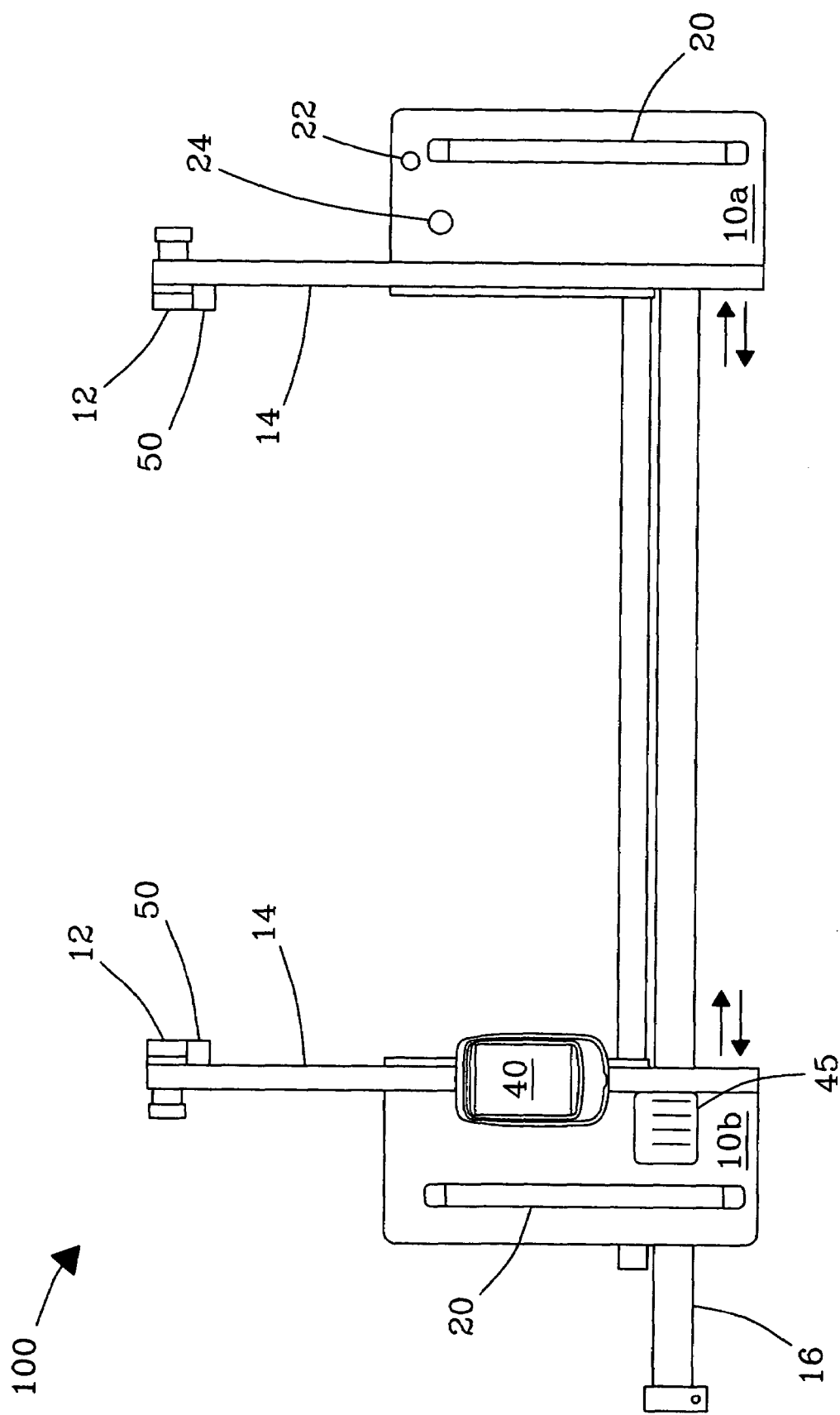
FIGS. 1a-1b illustrate two views of an inspection apparatus, a top-down horizontal view (FIG. 1a) and an isometric view (FIG. 1b), according to an embodiment of the invention.

An apparatus and method are disclosed for non-intrusive and non-invasive inspection of containers, materials, and/or fluids providing identification of the materials and/or fluids using multiple parameter acoustic signature inspection. The apparatus and method find application in such areas as process monitoring and control, chemical identification, shipping, contraband detection, and the like. For example, the invention is capable of detecting contraband and hidden compartments in fluid-filled containers with sizes in the range from about 1-inch to about 55-gallons. The invention is further capable of sorting fluids into groups of like and unlike, e.g., as between sweetened soda and diet soda. In addition, the apparatus and method permit identification of the fill-level in liquid-filled containers. No limitations are intended. The term "material" as used herein refers to a substance having characteristic, reproduceable, and/or ultimately measurable properties by which the material may be identified when an acoustic pulse or waveform is passed therethrough. Materials include, but are not limited to, e.g., homogeneous and inhomogeneous materials. Homogeneous materials include, but are not limited to, e.g., homogeneous liquids (e.g., tars), metals (e.g., aluminum, copper, steel), or the like. Inhomogeneous materials include, but are not limited to, e.g., mixtures, drugs, drug precursors, and the like. The term "fluid" as used herein refers to any substance having the capacity to flow or deform continuously under the action of a shearing or trangential stress regardless of how small the shearing stress may be. Fluids include, but are not limited to, e.g., liquids, low-viscosity liquids (e.g., water, milk), viscous liquids (e.g., tars), fuels (e.g., gasolines, diesels, kerosenes, derivatives thereof, or the like), oils (e.g., petroleum, lubricating, vegetable, or the like), compressed liquids (liquid propane, liquid nitrogen, etc.), derivatives thereof, or combinations thereof. No limitations are intended.

The term "waveform" as used herein refers to the shape of a pulse or signal in the time domain. More particularly, it is the observed pattern of the sound pressure variation displayed as a two-dimensional graph of pressure or amplitude against time, the shape of which is indicative of the frequency content of the waveform. Waveforms include, but are not limited to, e.g., square waveforms, triangle waveforms, sawtooth waveforms, and pulse waveforms. The term "pulse" as used herein refers to a segment or portion of a waveform, including both positive and negative frequency variations, e.g., as in an alternating or propagating waveform.

While much of the description of the invention will focus on operation related to inspection of materials and/or fluids within a container, the invention is not limited thereto. For example, the invention is adapted for inspection of and identification of bulk commodities including, e.g., tars, metals, and the like external to a container. The term "container", as used herein, means a receptacle for containing, holding, transporting, moving, and/or shipping of materials, fluids, liquids, compressed liquids, gases, bulk commodities, or combinations thereof, or the like. Containers may be of any type including, but not limited to, sealed containers, unsealed containers, shipping containers, transporting systems, pipelines, bulk material carriers, cargo containers, drums (e.g., 55-gallon drums), kegs (e.g., tar kegs), or the like. Containers may be composed of materials including, but not limited to, e.g., metal (e.g., Al, Cu, steel), plastic (e.g., HDPE), glass (e.g., glass containers, glass bottles, glass test tubes, glass cylinders, or the like), ceramics, or combinations thereof. The invention permits detection of anomalies and/or hidden objects or compartments in containers, as well as bulk solid commodities (roofing tar kegs or ingot of metal, e.g., Al, Cu, steel). The apparatus and method are further adapted for identifying contents of containers whether sealed or unsealed, open or shut, such that mislabeled containers and intentionally corrupted fluids as well as hidden contraband are readily discernible. A practical application of the invention is the examination of fluid filled containers for identification of the fluid. In other applications, the present invention provides for inspection and identification of material in a bulk commodity of material. The invention is not limited to inspection of any specific type, class, thickness, or size of container. The invention further can identify materials and detect contraband in the form of submerged packages and concealed compartments in liquid filled containers and/or solid-form commodities, and is adapted to rapidly interrogate outwardly innocuous containers and commodity items including, but not limited to, e.g., 5-gallon containers, test tubes, metal ingots, and the like. Other examples include open and unsealed drums or receptacles; closed and/or sealed drums or receptacles; open-air containers including hidden panel compartments within automobiles or other vehicles; cargo holds within transport vehicles or ships; receptacles for shipping, containing, or otherwise transporting bulk materials; flow structures and systems including tubing, piping, venting, etc.; process monitoring stations and systems. Also included are the wide diversity of containers used in the shipping and transport industries, including tankers, shipping containers, cargo containers (i.e., comex boxes), open-air cargo holds or other commodity transport compartments. It will also be apparent to those skilled in the art that, in its broader scope, a container may comprise a bulk material wherein a cavity or other chamber may exist. For example, a container may include the range of outwardly innocuous commodity items, such as metal ingots, with hollowed-out chambers, or tar kegs. Alternatively, a container may contain a bulk solid or a liquid wherein a sealed package containing contraband is concealed. Containers may comprise both single and multi-compartmented containment vessels. More complex containers may comprise a variety of process and/or flow systems or piping used for transporting or shipping materials. In the manual mode, the present invention is suited for the investigation of containers, vessels, chambers, or systems not easily interrogated or accessible because of size, depth, physical constraints, accessibility problems, commercial loads, physical encumbrances, lack of uniform dimensions, or other restrictions. Selection of the best target or location site for manual interrogation of the container is at the discretion of a user/operator. In some applications, an object may be concealed within a larger bulk material in a container. For example, a hidden package of contraband may be located within a bulk liquid or dry solid commodity, etc. In this instance, the ultrasonic pulse would reach the interface of the object within the bulk-contained material. As the object would be different from the bulk material, an acoustic echo would result at the interface of the object and the material. This early acoustic echo will reach the transducers prior to the time that the first acoustic echo reflected from the far container wall reaches the receiving transducer, permitting the object of interest to be ascertained and identified.

Inspection modalities (modes) used in conjunction with the invention will now be described.

Discrimination Modes

Acoustic Wave speed and Attenuation

The invention employs at least two principal discrimination modes for identification of materials and/or fluids: (i) acoustic wave speed, and (ii) attenuation. Acoustic wave speed (c) measures the time-of-flight of pulses traveling through materials and/or fluids being examined, e.g., a liquid-filled container. Attenuation, denoted by the coefficient of attenuation ($\alpha$), is a measure of acoustic losses or decreases in acoustic signal intensity. Both wave speed and attenuation are dependent on properties of the medium through which the pulse or waveform travels. Acoustic wave speed and attenuation of transmitted, received, or reflected pulses in a material or fluid are defined by equation [1]:

$$A = A_o e^{-\alpha z} \cos(kz - \omega t) \qquad [1]$$

where ($\alpha$) is the attenuation coefficient. The propagation constant (k) of the acoustic pulse or waveform propagating in the z-direction is determined from equation [2]:

$$k = 2\pi/\lambda = 2\pi f/c \qquad [2]$$

where ($\lambda$) is the wavelength, (f) is the frequency, and (c) is the phase wave speed. The radian frequency ($\omega$) is given by equation [3]:

$$\omega = 2\pi f \qquad [3]$$

Acoustic wave speed (c) may be calculated from equation [4]:

$$c = [(d/\text{Time-of-Flight})/2] \quad [4]$$

where (d) is the acoustic path length. Acoustic path length (d) and time-of-flight (TOF) of pulses traveling through, e.g., a container, a material or a fluid being examined are computed by the inspection apparatus.

Attenuation

The invention employs a relative acoustic attenuation as a secondary acoustic signature for discriminating between various fluids and materials. This "relative" attenuation coefficient ($\alpha$) is a "composite" measure of attenuation on acoustic amplitudes at the point and time of inspection, inherently accommodating acoustic losses from various energy loss mechanisms, e.g., in the walls and/or the geometry of a container, material, or fluid being inspected. The coefficient ($\alpha$) is calculated as the logarithm of the ratio of the amplitude of the acoustic pulse at two distances ($z_1$ and $z_2$) along the propagation path, as given by equation [5]:

$$A(f) = (\ln[A(f)_1/A(f)_2])/(z_2 - z_1) \quad [5]$$

where $A(f)_1$ and $A(f)_2$ are amplitudes received at positions $z_1$ and $z_2$, respectively. Consequently, determination of acoustic wave speed and attenuation is reduced to a measurement of time-of-flight and amplitude decay of acoustic pulses propagated through a container, a material, or a fluid. Equation [5] may also be expressed in terms of fast Fourier transforms as a function of frequency, as given by equation [6]:

$$\alpha(f) = (1/d) * \ln[FFT_2(f)/FFT_1(f)] \quad [6]$$

Despite the various complexities associated with energy losses in materials and fluids including, e.g., scattering, dispersion, and relaxation, a "composite", or relative, attenuation value can be measured for materials and fluids and as a function of time, temperature, and/or distance.

Temperature Dependence of Wave Speed and Attenuation

Acoustic wave speed and attenuation for materials and fluids vary as a function of temperature. For example, acoustic wave speed in water increases with increasing temperature. Errors in temperature for water at room temperature of as little as 0.1° C. can produce an error in wave speed of 0.3 m s$^{-1}$. Thus, temperature dependence of water can result in significant variations in the acoustic wave speed, requiring accurate measurement of the ambient temperature and accurate database information for comparison to field measurements. Acoustic wave speed and attenuation profiles of other materials and fluids also exist and can differ substantially or be very similar. Thus, algorithms that take temperature variations into consideration significantly improve measurement confidence and thus performance when identifying and/or discriminating between materials and/or fluids. For water, temperature dependence is given by equation [7]:

$$Vel_{water} = 1402.39 + 5.03711T - 0.0580852T^2 + 3.33420 \times 10^{-4}T^3 - 1.47800 \times 10^{-6}T^4 \quad [7]$$

Algorithms employed in conjunction with the invention compensate for known acoustic attenuation factors such as container wall composition (e.g., metals, glasses, ceramics, plastics), curvature of a container surface (e.g., flat versus curved). Further, corrections for container wall thickness may be ascertained and/or compensated for with suitable signal processing (e.g., TOF calculated from inner and exterior wall echoes) of acoustic pulses obtained therefrom. No limitations are intended by the current disclosure.

In principle, attenuation and wave speed parameters of any material and/or fluid may be compiled for use in conjunction with the invention without limitation. No limitations are intended. For example, parameters can be compiled, e.g., from reference sources or laboratory measurements providing an operator with the capability to accurately and precisely identify and discriminate between a wide variety of materials and fluids, including, e.g., chemical weapons, liquid explosives, contraband materials, dual-use materials, and/or other constituents and/or components.

Acoustic Coupling

To efficiently transmit acoustic pulses into a container, material, or fluid that propagate therein, adequate acoustic coupling is required. Factors influencing the accuracy of attenuation measurements include transducer coupling to the container, beam divergence, container type, distance (range) measurements, temperature measurements, transducer alignment, as well as frequency and bandwidth of the transducers. Container walls play a large role, in that varying materials will absorb varying amounts of acoustic energy. Container walls can also be flexible leading to incorrect distance measurements. In addition, container walls lead to variations in reflection coefficients, thereby changing the amount of energy transmitted through each interface. With advanced signal analysis, a compensation algorithm may account for energy transmission variations in and/or through various container walls of varying thickness. These limitations are overcome by accurately measuring distance between transducers in contact with a container or material instead of inputting a container size which can vary.

Transducer alignment is also important for accurate measurement of acoustic parameters. Transducers are opposed and aligned parallel to each other for accurate transmission and reception of acoustic pulses. With precise transducer alignment, distance determining means measures distance within strict tolerances.

As with wave speed, distance and temperature measurements are critical for accurate attenuation measurements. Divergence, or energy spread, is a phenomenon of acoustic waveforms whereby the energy spreads out as a function of distance from the source. The divergence error varies depending on the wave speed of the acoustic waveform in a material or fluid. This divergence of the beam spreads the energy over a larger area, which decreases the energy along the straight-line path between the transducers. Attenuation algorithms account for these changes in energy.

One embodiment of the invention will now be described with reference to FIGS. 1a-1b.

Figure 1B:
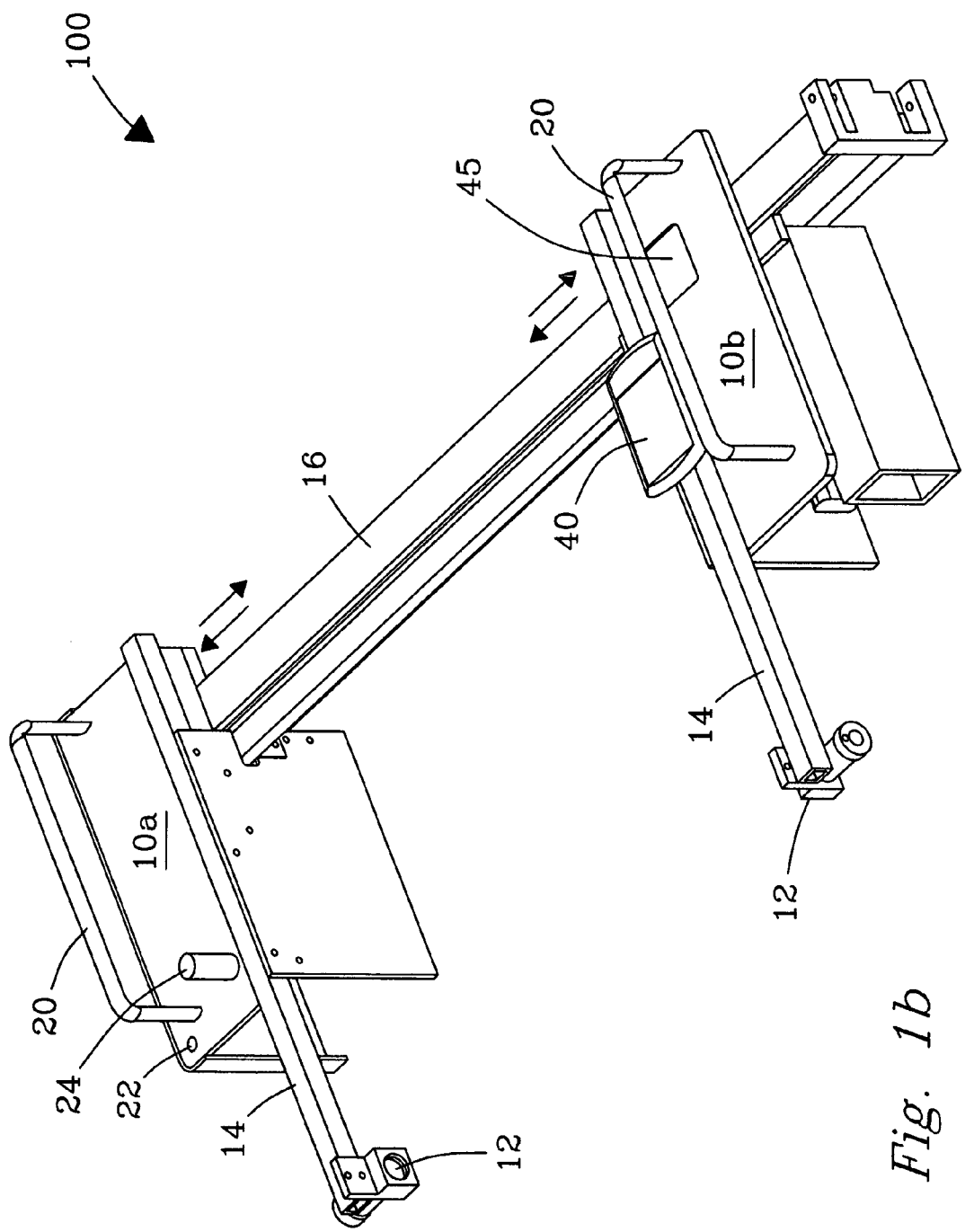

FIGS. 1a-1b illustrate two views of inspection apparatus 100 of a separable and portable design, according to one embodiment of the invention, a top-down horizontal view (FIG. 1a) and an isometric view (FIG. 1b). In the instant embodiment, the apparatus comprises two box portions 10a and 10b mounted to a support means 16 (e.g., frame) configured for extension and retraction along a horizontal axis for adjusting separation distance. Support means 16 may be any structure providing support for components of apparatus 100, including, but not limited to, e.g., frames, platforms, mounts, or the like. In other embodiments, support means can include flow systems, e.g., pipes or the like. No limitations are intended. A power switch 22 providing power to apparatus 100 is further located, e.g., on box portion 10b but is not limited thereto. A trigger (activation) switch 24 is further mounted e.g., to box portion 10b, but again is not limited. In the instant embodiment, trigger 24 is located near handle 20 so as to be accessible by a person grasping handle 20. When trigger 24 is activated by a user/operator, a signal (e.g., TEST) sent to microcontroller 250 initializes inspection apparatus putting it in "ready" mode.

In the instant embodiment, at least two transducers 12 are mounted at the ends of substantially parallel exension members 14 (arms) attached to respective box portions 10a and 10b so as to be opposed to one another, the distance between the transducers 12 being selectable by extending the left and right box portions 10a and 10b of inspection apparatus 100 along its mounting frame (i.e., extension rack). Handles 20 are mounted to the top of each box portion 10a and 10b for adjusting same. Transducers are in vertical and horizontal alignment with such that the inspection heads are opposed for contacting and coupling to container surfaces.

In the instant embodiment, a computing means 40 is mounted to the upper surface of one of box portions 10a or 10b, appropriately positioned to be observed by a user/operator. Computing means 40 handles all data processing, analyses, calculations, algorithms, including interface management, data storage, as well as operator inputs/commands/instructions. No limitations are intended. Computing means includes systems and computing devices selected from, but not limited to, e.g., portable computers, handheld computers, tablet PCs, Personal Digital Assistants (PDAs), laptops, desktops, mainframes, including components, circuits, and associated systems thereof. In the instant embodiment, computing means 40 is a Tablet PC (e.g., a model LS800) available commercially (Motion Computing, Austin, Tex., USA) comprising a 1.2 GHz Pentium® processor, 1 GB RAM, 1 GB ROM, and standard operating software, but is not limited thereto.

Computing means 40 is further equipped with a "View Anywhere Display" for displaying data, visual indicators, results, values, and like data/information. Computing means further includes a user interface by which any selected parameters and/or variables can be controlled or input by a user/operator. Any suitably defined user-interface can be used (e.g., a Windows XP or Linux operating system) as will be selected and implemented by those of skill in the art. Thus, software platform is not limited. Input variables for selection by a user/operator include, but are not limited to, e.g., waveform amplitude, excitation frequency, pulse width, digitization rate, and like parameters, and combinations thereof. For example, ultrasonic waveforms and/or data can be displayed to a user/operator. Computing means also has the capability of displaying parameters of the received pulses and/or waveforms, including, but not limited to, e.g., threshold levels, noise levels, backgrounds, and the like further providing capabilities for selecting portions (i.e., gating) of a waveform for subsequent waveform analysis and/or examination. Other indicators displayed by computing means include, but are not limited to, e.g., activation of the apparatus, power to the apparatus, component disconnects, low battery, and errors encountered during operation of the inspection apparatus. Computing means is further optionally configured to provide auditory (e.g., alarms) prompts to a user.

In other embodiments, computing means may be a dumb terminal, e.g., an embedded dumb terminal. In other embodiments, computing means may be carried by a user/operator, e.g., on a belt, for portable deployment. In another embodiment suited to automated processes such as system monitoring and/or control applications, computing means may be a laptop or a desktop computer or system, or alternatively a mainframe, a server, or a like computer system. In one exemplary configuration, computing means is, e.g., a laptop deployed separately or at a distance from inspection apparatus, e.g., for operation in conjunction with a flow system operation or application, e.g., mounted to the outside of a pipe or like flow system allowing for inspection and/or identification of contents therein in real-time.

In one embodiment, computing means 40 is in electrical communication with circuit (signal conditioning) means 200 via a Net Burner interface and a standard Ethernet cable. In another embodiment, electrical communication is provided by, e.g., a compact flash card insert on a Tablet PC. In the instant embodiment, circuit means (described further in reference to FIG. 2) mounts within box portion 10b, as illustrated in FIG. 1b, but is not limited.

Transducers

Transducers 12 of the inspection apparatus 100 transmit and receive waveforms through a container, material, or fluid for inspection of same. The term "transducer" as used herein refers to a device for transmitting, receiving, and/or measuring ultrasound. Transducers are selected having a broadband range of frequencies applicable to the expected variety of materials and fluids inspected. Frequency choices depend on factors, including, but not limited to, dimensions of a container being examined, materials, fluids, temperature or other ambient environmental conditions, rheologic and acoustic properties of the material, and the like. Frequency selected for transducers may be varied depending on the container, material, or fluid to be inspected, as will be understood by those of skill in the art. Number of transducers is not limited. In one embodiment, inspection apparatus employs small diameter (nominal diameter of ~0.5 inches), high-bandwidth, high-frequency transducers, but is not limited thereto. Transducers have a leading contact surface for contacting a container or material being inspected. Transducers operable in inspection apparatus do not require use of "acoustic contacting gels" because dry coupling means 55 attached to each transducer provides high efficiency for signals, waveforms, or pulses into a material, fluid, or container. Crystal elements of the transducers are of a piezo-composite ceramic or magnetostrictive type to generate desired broadband characterstics of the acoustic pulses. In the instant embodiment, transducers have a center frequency in the range from about 1 MHz (e.g., AGFA Model 389057-070, GE Inspection Technologies, Lewistown, Pa., USA) or 5 MHz (e.g., AGFA Model 389057-080, GE Inspection Technologies, Lewistown, Pa., USA). Lower ultrasonic frequencies provide increased penetration in highly attenuative, inhomogeneous liquids and/or materials (e.g., oils, molasses). In general, low-frequency acoustic pulses travel further than high-frequency acoustic pulses and are thus preferably used to inspect larger containers. Higher frequencies provide for increased resolution and greater measurement sensitivity suitable for less attenuative, homogenous liquids and/or materials. High-frequency transducers, e.g., can be used to inspect both small and large containers, e.g., 55-gallon drums containing a bulk fluid or material, unless other attenuation factors must be considered. Transducers can be used as receiving transducers, transmitting transducers, or in various transmitting/receiving combinations in conjunction with the various operational modes employed by inspection apparatus, as described herein. No limitations are intended.

Coupling Means

Coupling means 55 couples transducers to a container, material, or fluid for inspection thereof. Preferred couplants do not require use of a wetting agent or gel for contacting a container or material being inspected. In one embodiment, the coupling agent is a dry coupling agent. Dry coupling materials include those composed of low-attenuation elastomers, e.g., Aqualene® (R/D Tech, 505, boul. Du Parc-Technologique, Quebec, Conn.), having an acoustic impedance nearly identical to that of water with an upper useful temperature of around 200° C. that can transmit frequencies up to about 25 MHz in a longitudinal waveform. Acoustic impedance of a dry coupling material is selected in the range from about 1.0 g cm$^{-2}$ sec$^{-1}$×10$^5$ to about 4.0 g cm$^{-2}$ sec$^{-1}$×10$^5$. Longitudinal acoustic wave speed for a dry coupling material ranges from about 0.05 inches per microsecond to about 0.085 inches per microsecond. Densities of dry coupling materials range from about 0.9 g/cm$^3$ to about 3.5 g/cm$^3$. Material hardness varies from about 40A ("soft") to 70A ("hard") durameters. Physical property information for Aqualene®, a representative dry coupling material is listed in TABLE 1.

TABLE 1

Physical and acoustic properties for Aqualene ®, a representative dry coupling material.

| Density | L-wave (longitudinal) acoustic wave speed | Shear wave acoustic wave speed | Attenuation (L-wave) | Characteristic Impedance |
|---|---|---|---|---|
| 0.92 kg/m$^3$ | 1590 m/s | 800 m/s | 0.28 dB/mm @ 5 MHz | 1.49 Mrayls |

| Poisson's Ration | Young's Modulus | Modulus of Shear | Transmission Coefficent (L-wave from H20) | Opacity |
|---|---|---|---|---|
| 0.329 | 1.577 × 10$^9$ Pa | 0.593 × 10$^9$ Pa | 0.984 | Clear to slightly translucent |

Dry coupling means 55 is applied to the contacting face of the selected transducer 12 using an affixant (tapes, epoxies, resins, or the like) thereby providing high acoustic efficiency for transmitting waveforms from the inspection apparatus through a container, material, and/or fluid being inspected. Selected dry coupling means are sufficiently yielding to conform to the surface of container or material being inspected.

Other couplants, while not optimum, can be used including, but not limited to, e.g., neoprene, solid water, aqueous bacteriostatic standoff materials, including, e.g., Aquaflex® (Parker Laboratories, Inc., Fairfield, N.J., USA), silicone rubber, room temperature vulcanizing (RTV) silicone rubber, butyl rubber, urethane, polyurethane, thermoplastic urethane, Ecothane® (Optimer, Inc., Wilmington, Del., USA), Pellathane® (Optimer, Inc., Wilmington, Del., USA), or the like. No limitations are intended. Couplants in this group have a thickness in the range from about 0.635 mm (0.025") thick to about 2.3 mm (0.091") thick. More particularly, thicknesses are selected in the range from about 0.03 inches to about 0.4 inches. Thickness depends in part on inspection conditions and the surface configuration of the material or container being inspected. Thus, no limitations are intended. For example, where irregularities or reverse curves in the surface or container being inspected exist, thickness can be altered better conforming to the container surface.

Additional coupling materials include water, oils, jellies, Vaseline®, polymer bounded structures (e.g., rubber balloons) filled with, e.g., water/alcohol. All coupling agents as will be contemplated and implemented by those of skill in the art are encompassed herein.

Path Length Measuring Means (45)

Inspection apparatus 100 is configured with a path length (PL) measuring means 45 for measuring acoustic path length (d) and/or distance through a container. Measuring means include, but are not limited to, e.g., calipers, encoders, micrometers, lasers, acoustic cameras, or the like. PL-measuring means 45 provides an output corresponding to the measured path length or distance to computing means 40 that is used in various algorithms, e.g., time-of-flight determinations and for numeric or digital display to a user/operator. Location of the PL-measuring means is not limited. In the instant embodiment, PL-measuring means is a caliper coupled to supporting means 16.

PL-measuring means is electrically connected to circuit means 200 (described hereafter with reference to FIG. 2) providing path length data to computing means 40.

Temperature Measuring Means (50)

The inspection apparatus is configured with a temperature measuring means 50 that ascertains temperature (T) of the quantity of material in a container or material being inspected. Temperature is provided as an output (e.g., analog, digital, or numeric) to computing means 40 for numeric display to an operator and/or incorporation into temperature-dependent algorithms. Inspection apparatus employs at least two temperature measuring means providing an average temperature for a container, material, or fluid being inspected thereby enhancing accuracy and precision for measured temperatures. Temperature measuring means include, but are not limited to, e.g., thermometers, pyrometers, infra-red devices, thermocouples, sensors, detectors (e.g., resistance temperature detectors or RTD's), thermistors, including components and circuits thereof, or the like. In one embodiment, temperature measuring means are optical infra-red pyrometers coupled to each transducer 12 of inspection apparatus. Location of temperature measuring means is not limited, but is preferably positioned in close proximity to transducers for accurate acquisition of temperature. In the instant embodiment, temperature measuring means couple electrically to the inspecting end of each transducer.

Temperature measuring means is electrically connected to circuit means 200 (described hereafter with reference to FIG. 2) providing temperature data to computing means 40.

Circuit (signal conditioning) means 200 of inspection apparatus 100 will now be described in further detail with reference to FIG. 2 hereafter.

Circuit (Signal Conditioning) Means (200)

Figure 2:
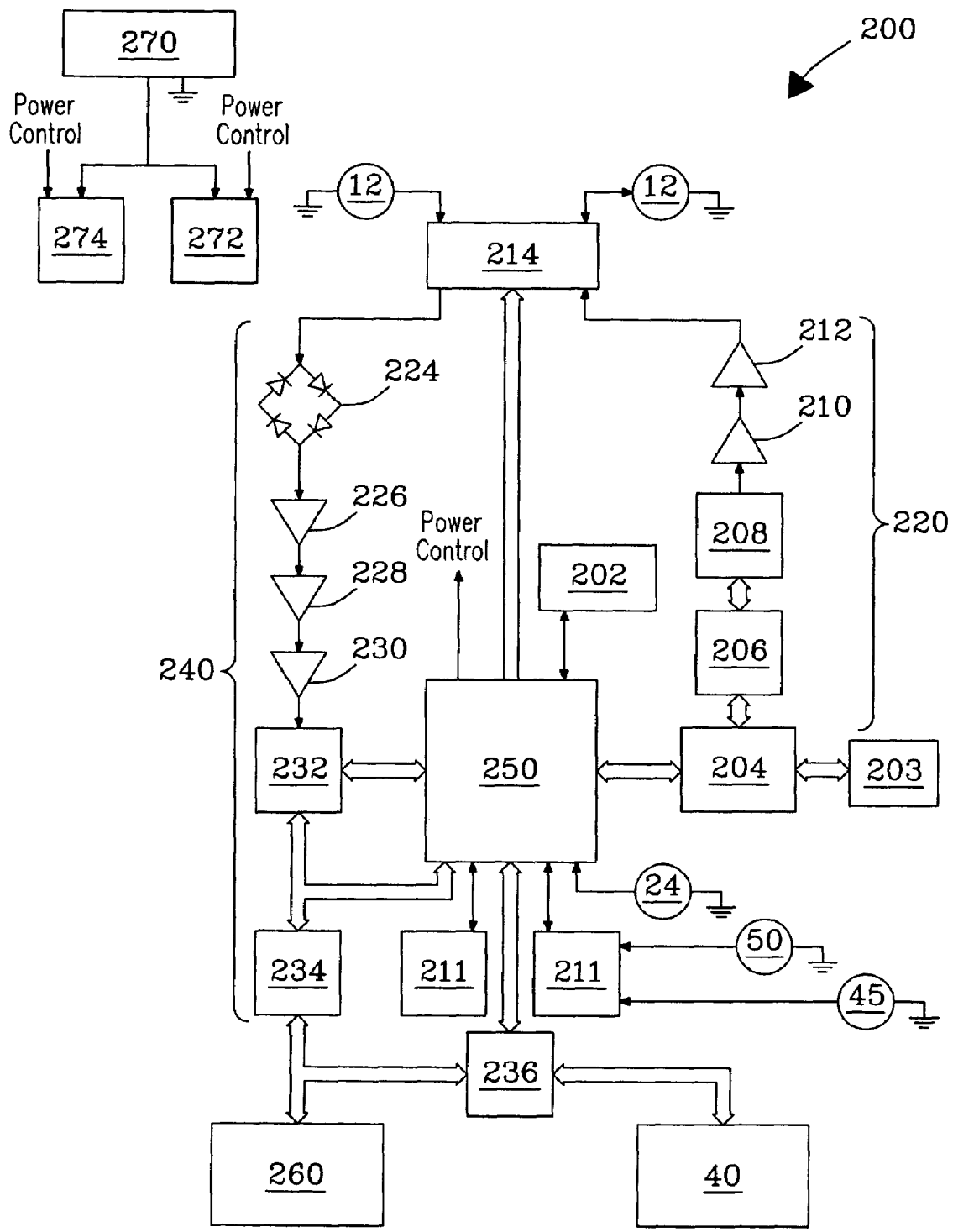
FIG. 2 is a block diagram illustrating a circuit (signal conditioning) means for generating and conditioning pulses, waveforms, and/or signals, according to an embodiment of the invention.

FIG. 2 is a block diagram illustrating a circuit (signal conditioning) means 200 for generating and conditioning waveforms, pulses, and/or signals, according to an embodiment of the invention. The term "signal conditioning" as used herein refers to any of a multitude of signal processing and conditioning functions known to those of skill in the art, including, but not limited to, e.g., amplifying, attenuating, biasing, bridging, buffering, comparing, converting, digitizing, driving, filtering, gating, increasing, integrating, processing, rectifying, squaring, transmitting, windowing, or the like, or combinations thereof. Signal conditioning encompasses all circuits, circuit components, devices, equipment, and/or systems providing desired signal, waveform and/or pulse characteristics, including, but not limited to, e.g., frequency, impedance, shape (e.g., square, triangle, etc.), current, voltage, timing, and the like, or combinations thereof. Circuit means 200 provides signals, waveforms, and/or pulses transmitted by, and/or received by, inspection apparatus 100 in a format suitable for circuit means 200, including circuits, components, or systems coupled thereto. Components, circuits, or systems include, e.g., signal conditioning circuits, comparators, amplifiers (e.g., gated current-to-voltage amplifiers, sample-and-hold amplifiers, operational amplifiers, linear amplifier, non-linear amplifiers, or the like), switches (e.g., mechanical, pushbutton, toggle, trigger, logic, flip-flop latch, or the like), multiplexers, filters (e.g., low-pass filters, high-pass filters, or the like), oscillators (e.g., application to interval timers, or the like), interfaces (e.g., transducer interfaces), analog-to-digital converters (ADC) and allied circuits (e.g., parallel encoding, flash, successive approximation, dual slope, or the like), digital-to-analog converters (DAC) and allied circuits (e.g., current summing, switched current devices, or the like), encoders, digitizers, data acquisition (DAQ) circuits and devices (e.g., plug-and-play, multiplexers, load cell input, DRF-IDC, DRF-IAC, DC and AC Current Input Signal Conditioners, DRF-VDC and DRF-VAC, DC and AC Voltage Input Signal Conditioners, DIN-rail mounted devices, Isolators, Transmitters and Alarms, and other related components (e.g., AC, DC, Pot, Bridge, RTD, TC inputs, or the like), including associated firmware and/or hardware. Operational amplifiers, for example, are suitable for increasing amplitudes of a signal, filtering a signal, decreasing signal output impedances, providing variable gain and offset controls, and/or calibrating output signals from the transducers. In a simple configuration, for example, signal conditioning typically occurs in the interface between, e.g., an electrical circuit and the signal transmitting (output) device [e.g., between the circuit (signal conditioning) means and the transmitting transducer (output)], or between the signal receiving (input) device and an electrical circuit, e.g., the transducers (input) and circuit (signal conditioning) means. All signal conditioning components, devices, and/or systems as will be implemented by those of skill in the art are within the scope of the disclosure. No limitations are intended.

Pulser Section (220)

Circuit means 200 comprises a pulser section 220 that provides an excitation (transmission) waveform or pulse transmitted by a transmitting transducer 12 for inspection of a container, material, or fluid. Pulser section includes a Field Programmable Gate Array (FPGA) 204, (Pulser) FIFO 206, (Pulser) Digital-to-analog Converter (DAC) 208, (Pulser) current-to-voltage converter (Buffer) 210, (Pulser) Power Amplifier 212, multiplexer 214, and transducer 12 (e.g., a transmitting transducer). Components of the Pulser section couple electrically to microcontroller 250. Microcontroller 250 further links to an EEPROM 202, and RAM or ROM 203 that store digital waveform data and configuration information, respectively. Pulses or waveforms stored in the EEPROM are provided to FPGA 204 by command from microcontroller 250 and into the Pulser FIFO. The digital waveform undergoes subsequent conversion to an analog waveform in the DAC 208 with appropriate current-to-voltage conversion in the Buffer component 210. The transmission waveform (chirp) is amplified to the appropriate transmission frequency in the Power Amplifier 212 component. Multiplexer 214 sets the operational mode [pitch-catch (P/C) or pulse-echo (P/E)] of the inspection apparatus as selected by a user/operator, with transmission of the excitation waveform (chirp) by the transmitting transducer 12. Components of Pulser section 220 are described in more detail hereafter.

FPGA (204). The Field Programmable Gate Array component (e.g., a model EPM7128AETC1005 FPGA chip, Altera Corp., San Jose, Calif., USA) is electrically coupled to microcontroller 250. FPGA is a logic circuit that controls the loading of the digital waveform (excitation chirp) stored by the EEPROM 202 into the Pulser FIFO 206. FPGA further provides waveform control functions including, but not limited to, e.g., delay time, digitizing rate, and other logic functions of the circuit means. For example, the FPGA communicates/interacts with microcontroller providing operator control and/or configuration data to apparatus 100. In this manner, operation parameters including, e.g., pulse width, timing, delivery, and frequency of pulses are communicated to the inspection apparatus. FPGA further governs the amplification of the waveform by Power Amplifier 212 and frequency selection (e.g., high or low) dispositioning the excitation waveform for transmission by a transmitting transducer 12. FPGA further controls data transfer to and from EEPROM 202. FPGA operates in conjunction with an encoded programming language, e.g., Very High Speed Integrated Circuit Hardware Description Language (VHDL), the language providing coding and control of logic functions, including those allied functions used to transfer and retrieve the transmission waveform. Waveform data are transferred from the EEPROM through the microcontroller to the FPGA. When trigger 24 is activated, the analog equivalent of a waveform is requested by command from microcontroller 250. FPGA retrieves the stored waveform from EEPROM 202, and sends the digitized waveform to DAC 208 for conversion to an equivalent analog waveform (CHIRP). Waveform data are buffered to FPGA 204 to Pulser FIFO 206. The term "buffer" and "buffering" as used herein refers to the parsing or transferring of data from or to coupled circuit components providing waveform data at suitable clock speeds to the intended components.

Pulser FIFO (206). Pulser FIFO 206 is operatively connected to the FPGA component 204 and microcontroller 250 to computing means 40. The Pulser FIFO buffers digital waveform data to the Digital-to-analog converter (DAC) 208 for conversion to its analog form.

Pulser DAC converter (208). Circuit means 200 further includes a Digital-to-Analog converter (DAC) 208 (e.g., a model ISL5761/21B DAC, Intersil Corporation, Milpitas, Calif., USA). In the instant embodiment, the DAC is a 100 MHz, 10-bit D/A converter. The DAC has an operative connection to microcontroller 250 and is powered by a voltage received from regulator 272. The DAC provides current outputs that are converted to voltages in Buffer (current-to-voltage converter) component 210, described hereafter.

Pulser Buffer (210). Circuit means 200 further includes a Pulser Buffer (current-to-voltage converter) 210 (e.g., a model AD847 high speed, low power operational amplifier, Analog Devices, Norwood, Mass., USA). In the instant embodiment, the Buffer has a full-power bandwidth of 12.7 MHz (5V peak-to-peak with ±5 V supplies). Buffer converts the current output from DAC 208 and provides an voltage output to Power Amplifier 212. Current outputs (I_OUT_A and I_OUT_B) from DAC converter 208 are converted to voltages through the current-to-voltage converter component 210 and amplified by the Power Amplifier 212, described hereafter.

Pulser Power Amplifier (212). Pulser section 220 further includes a Power Amplifier 212 (e.g., a model AD815ARB-24 Power Amplifier, Analog Devices, Norwood, Mass., USA), which provides the waveform output from Pulser Buffer 210 with a proper output voltage (e.g., 4 V). In the instant embodiment, Power Amplifier provides a waveform ("chirp") having a wide bandwidth of up to 10 MHz (4 V peak-to-peak) and low harmonic distortion suitable for transmission by transmitting transducer 12.

Figure 3:
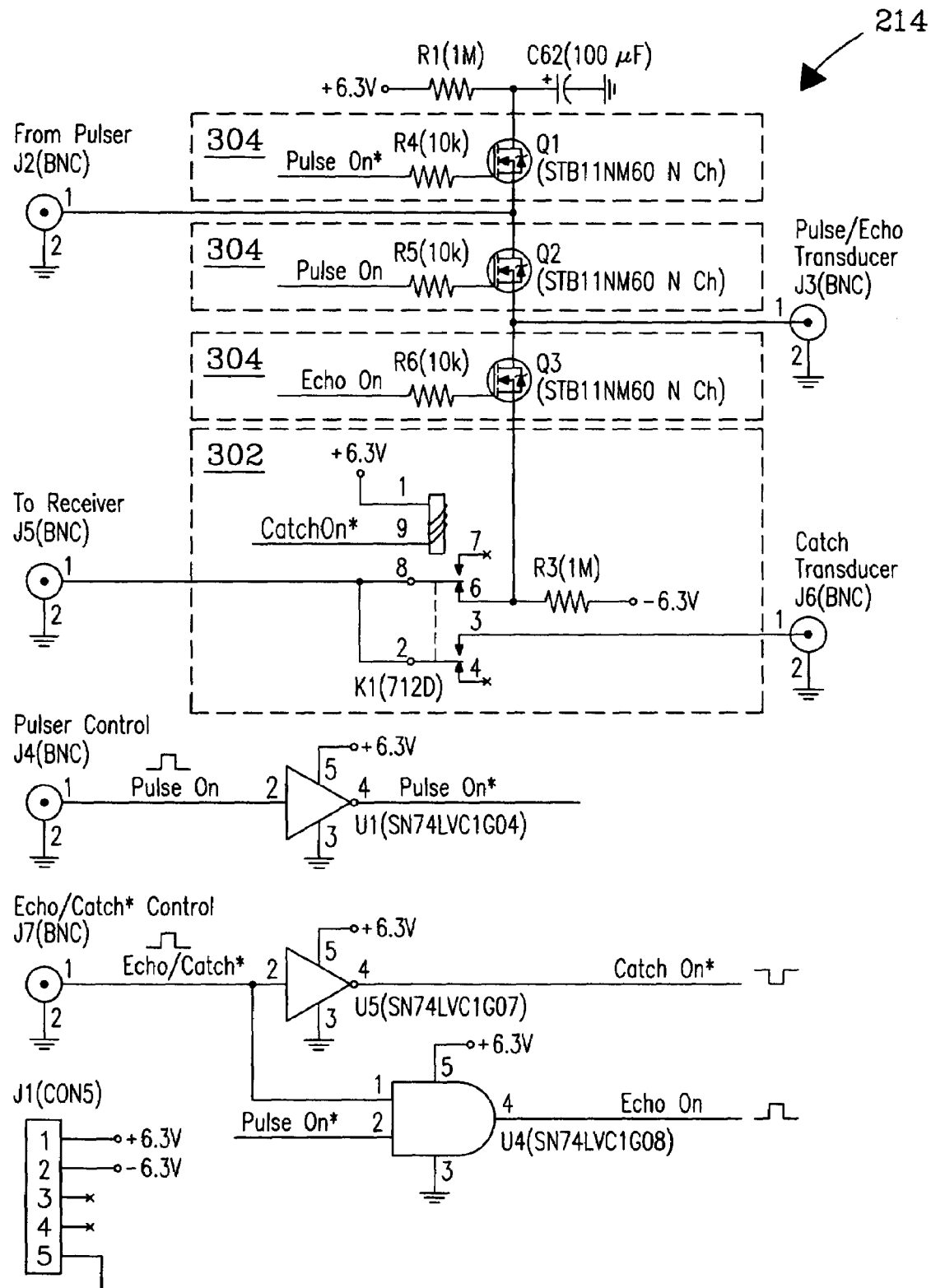
FIG. 3 is a circuit diagram for a multiplexer that provides rapid switching between transducer operational modes, according to an embodiment of the invention.

Multiplexer (214). Pulser section 220 employs a Multiplexer 214 as the mode switching component for rapid switching between operational modes (e.g., pitch-catch and/or pulse-echo) of the transducers 12 in inspection apparatus 100. In the instant embodiment, multiplexer 214 is a uniquely configured combination circuit (illustrated in FIG. 3) that includes a Relay 302 (e.g., a model 712D Relay, Teledyne, Hawthorne, Calif., USA) and one or more electrically coupled Power MOSFET switches 304 (e.g., model STP11 NM60 Power MOSFETs, STMicroelectronics, Dallas, Tex., USA) permitting rapid switching between pulser section 220 and receiver section 240 (described further below) isolating the receiver from the pulser, and rapid switching between pitch-catch and pulse-echo inspection modalities. Multiplexer receives high voltage inputs from Power Amplifier 212 providing rapid power-on frequencies up to 10 MHz (4 V peak-to-peak) to the excitation waveforms (chirps) transmitted by a transmitting transducer 12. The amplified, encoded waveform (chirp) is transmitted into the container, material, or fluid being inspected by command (e.g., "FIRE") from the microcontroller 250.

Receiver Section (240)

Analog waveforms transmitted through a container, material, or fluid from an inspection are received by one or more transducers 12 (e.g., receiving transducers) in receive mode (in any of Pulse-Echo and/or Pitch-Catch operational modes) to Receiver Section 240 of circuit means 200. Receiver section 240 includes the receiving transducers 12, multiplexer 214, (Receiver) Peak Conditioning circuit 224, (Receiver) pre-amp 226, (Receiver) filter section 228, time-variable gain circuit (e.g., TVG) 230, (Receiver) ADC 232, and (Receiver) FIFO 234. Components in Receiving Section 240 electrically connect with microcontroller 250. A received waveform is provided as an input (e.g., UT_SIG_RAW) to Peak Conditioning Circuit 224 where the waveform is conditioned (e.g., a bias voltage applied). The conditioned signal is preamplified by the pre-amp component 226 and subsequently provided to a Filtering component where waveform noise is filtered and removed. The waveform is then amplified (e.g., via GAIN_SET command) from microcontroller 250 in a time variable gain circuit 230 and subsequently digitized in the Receiver ADC 232. The digitized waveform is next provided to the Receiver FIFO 234 and subsequently buffered in conjunction with a Tri-State buffer circuit 236 under command of microcontroller 250 to Net Burner interface 260, where it is appropriately packaged for transport to computing means 40 for further processing. Components of Receiver Section 240 will now be described more particularly hereafter.

Peak Conditioning Circuit Section (224). Analog signals received by a receiving transducer 12 to Receiver Section 240 are first input to Peak Conditioning Circuit 224. Conditioning Circuit is of a simple biasing design that includes: 1) a capacitor (e.g., a de-coupling capacitor), in series, that blocks all DC current allowing received analog (AC) signals to pass; 2) two resistors coupling at a junction, a first resistor connecting to ground and a second resistor acting as a voltage divider. The voltage divider provides a DC bias at the resistor junction of, e.g., +5 V (half the input voltage); and, 3) two diodes that remove, and thus protect, Receiver Section 240 from voltage spikes. Conditioning circuit provides peak conditioning and a bias voltage of +5 V to Pre-Amp component 226, described hereafter.

Pre-Amp (226). Receiver Section 240 further includes a Pre-Amp component 226 (e.g., a model AD8009 Operational Amplifier, Analog Devices, Norwood, Mass., USA). In the instant embodiment, the operation amplifier is of a high bandwidth product design, permitting amplification to be yet applied to any high frequency waveforms received (up to 10 MHz). The pre-amp provides sufficient amplification (e.g., of up to +6 dB) to the raw waveform whereby noise can be filtered and removed in the Bandpass Filter section 228, described hereafter.

Bandpass Filter (228). Receiver Section 240 further includes one or more Bandpass Filters 228 (e.g., a model AD8009 Operational Amplifier, Analog Devices, Norwood, Mass., USA). Bandpass filters include, but are not limited to, e.g., Highpass Filters (HPF) and Lowpass filters (LPF). In the instant embodiment, the Bandpass Filter Section 228 includes two Low Pass (+6 dB) Filters in series, but is not limited thereto. The filters remove noise from the raw waveforms, yielding waveforms with a high signal-to-noise ratio. Waveforms are subsequently provided to the TVG 230, described hereafter.

TVG (230). Waveforms output from the Filter section 228 are received into the Time-Variable Gain (TVG) component 230 (e.g., a model AD9432 TVG, Analog Devices, Norwood, Mass., USA). The TVG provides attenuation or amplification factors as needed to optimize waveforms provided to computing means 40. When a weak signal is received from a receiving transducer 12, as for example, when a received waveform is highly attenuated due to its passing through a long distance, microcontroller 250 automatically requests an increase in waveform amplitude by increasing the voltage set by TVG 230 in receiver section 240 and again transmits a waveform (chirp) through pulser section 220. The received signal is reprocessed in receiving section 240 until amplitude is optimized. A user/operator can also manually request an increase in waveform amplitude via the user interface of computing means 40. If amplitude is too large (e.g., saturated), microcontroller 250 automatically requests a decrease in waveform amplitude and lowers the voltage set by TVG 230 in receiver section 240. Microcontroller 250 monitors the waveform amplitude in the Received ADC 232, described hereafter.

(Receiver) A/D Converter (232). Receiver Section 240 further includes a Receiver Analog-to-Digital (A/D) converter 232 (ADC) (e.g., a model AD9432 ADC, Analog Devices, Norwood, Mass. USA). The A/D converter has an operative connection to microcontroller 250 and is powered by a voltage from regulator 272. The Receiver ADC serves a principal function of providing digitized waveforms to computing means 40 for further processing. In the instant case, ADC provides a 100 MHz sampling rate at a 16-bit resolution, but is not limited thereto. The ADC has an operative connection with microcontroller 250, which monitors amplitude of the digitized waveform, as described herein. If the waveform amplitude is too large (i.e., saturated), a flag in the ADC informs the microcontroller, which then lowers the gain setting in the TVG 230 as described previously. If the waveform amplitude is too small, the microcontroller raises the gain setting in the TVG, optimizing the waveform provided to computing means 40. Thus, the ADC provides for an enhanced digital dynamic range and improved resolution for received waveforms in both the time and frequency domains. Size (e.g., number of bytes in the waveform) or samples per waveform is variable.

(Receiver) FIFO (234). Receiver Section 240 further includes a Receiver FIFO 234 (e.g., a model CY7C4285-10ASC FIFO, Cypress Semiconductor, San Jose, Calif., USA) for buffering waveform data from the ADC 232. In the instant embodiment, Receiver FIFO is currently a 16-bit component having two bus elements, but is not limited thereto. Receiver FIFO electrically couples with microcontroller 250, Net Burner™ 260, Tri-State Buffer 236, and computing means 40 providing waveform data in a suitable format to computing means 40 via an Ethernet cable (not shown) for further processing. Input/Output (I/O) over the various bus elements of circuit means 200 are regulated and/or controlled in conjunction with Tri-State Buffer circuits 236 (e.g., a model 74VCX16244DT 16-bit, +3.3 V 3-State Buffer, ON Semiconductor Corp., Phoenix, Ariz., USA). Receiver FIFO operates on a "first-in/first-out" basis allowing data to be input at a fast rate and to be extracted at a slower rate, i.e., upon request. Waveform inputs to Receiver FIFO come from analog-to-digital converter 232. When Receiver FIFO buffer is ready, waveform data are retrieved, read, and transmitted via a parallel data bus to Net Burner™ interface and microcontroller 250.

Microcontroller (250)

Microcontroller 250 (e.g., a model MSP430F169 microcontroller chip, Texas Instruments, Dallas, Tex., USA) is a command center of circuit means 200 providing for processing and transmission of waveform data to and from computing means 40. Functions of the Microcontroller include, but are no limited to, e.g., receiving, processing, transferring data and information to and from circuit means 200. Microcontroller further processes configuration, setup, and/or command information received from the user interface of the computing means. For example, microcontroller is operative for receiving user commands input from computing means that control delay time, digitizing rate, pulse width frequency, or other user controlled functions. Configuration information is transmitted through Net Burner™ 260 to Microcontroller where it is written and/or stored to the EEPROM 202 (described further hereafter) providing user configuration commands and/or information to the inspection apparatus 100. Once received, microcontroller returns updated configuration information (e.g., from EEPROM 202), along with any updated temperature readings from temperature means 50 and distance readings from distance measuring means 45 back to computing means 40. Microcontroller further provides transfer of waveform data to and from Net Burner interface 260. Digitized waveform data from the ADC 232 are transmitted through Net Burner™ interface 260, which packages and prepares data with proper Ethernet protocols (TCP/IP or UDP), including protocol requirements, header information, and packet format, etc. for transfer to computing means, where waveforms are reassembled and/or data are further processed. Microcontroller 250 is further responsible for initiating and synchronizing pulser circuit 220 that results in transmission of the excitation waveform. Microcontroller 250 further processes waveform data received through Receiver section 240.

EEPROM (202)

Circuit means 200 further includes an EEPROM 202 (e.g., a model 24LC64SN 64K EEPROM chip, Microchip Technology, Inc., Chandler, Ariz., USA), a non-volatile memory component for storing the encoded digital transmission waveform (Chirp) until requested by microcontroller 250. The EEPROM further stores operational settings and setup information for inspection apparatus 100.

The digital waveform (CHIRP) stored in the EEPROM is provided from Pulser FIFO 206 to (Pulser) DAC converter 208 whereby the digital waveform is converted to its analog form. Buffering from the (Pulser) FIFO 206 can be further assisted in conjunction with a Tri-state Buffer component 236.

RAM (203)

RAM Component (203). Circuit means 200 further comprises a RAM component 203 having operative connections with microcontroller 250, FPGA 204, FIFO 206, and computing means 40. The RAM component is a temporary memory and data exchange location. The RAM component uniquely identifies, directs, and/or stores the various "chirp" configurations or waveforms temporarily. User commands and/or requests input by an operator via computing means 40 are stored in the RAM component. Waveform data stored in the RAM component are transmitted to, and buffered by, the (Pulser) FIFO component.

Net Burner Interface (260)

Net Burner interface 260 (e.g., a model 5272 Net Burner interface, available from Net Burner, Inc., San Diego, Calif., USA or Lightner Engineering, La Jolla, Calif., USA) is a communication interface providing (e.g., signal) data or information (e.g., user commands/input) between circuit means 200 and computing means 40. Net Burner is currently an Ethernet server communication board having a 16-bit data acquisition resolution, but is not limited thereto.

Path Length Measuring Means (45)

Path Length Measuring Means 45 (e.g., a caliper) includes an independent analog-to-digital (A/D) converter that converts analog path length outputs to digital values representative of collected distance readings. PL sensor A/D communicates with microcontroller 250 via an RS-232 circuit 211. Microcontroller automatically and periodically interrogates the path length measuring device and transmits the digitized values to Net Burner 260 where data are packaged and transmitted via Ethernet to computing means 40. Path Length may also be manually requested by a user/operator through the user interface of computing means 40.

Temperature Measuring Means (50)

Temperature measuring means 50 (temperature sensor) includes an independent analog-to-digital (A/D) converter for converting analog temperature outputs (e.g., THERMISTER_H) to digital values representative of collected temperature readings. Temperature sensor communicates with microcontroller 250 via an RS-232 circuit 211 providing digital temperature data thereto. Microcontroller 250 automatically and periodically interrogates temperature sensor and transmits the digitized temperature values to Net Burner 260 where data are packaged and transmitted via Ethernet to computing means 40. Temperature may also be manually requested by a user/operator through the user interface of computing means 40.

Power Supply/Removable/Rechargeable Battery

Power supply 270 provides power for operation of inspection apparatus 100. In the instant embodiment, Power Supply is a battery (e.g., a 7.4 V, 4.4 Amp hours battery), providing for field deployment and/or portable operations of inspection apparatus, but is not limited thereto. For example, in other embodiments, power supply may be a direct electrical source for use in real-time process monitoring and/or control operations. No limitations are intended. As will be understood by those of skill in the art, the invention can be configured with many system and/or process components.

Regulator/DC-to-DC Converter

Power regulator 272 and DC-to-DC converter 274 provide voltages to individual components of circuit means 200 from a power source (e.g., a battery or other power source) 270. For example, regulator provides various voltages (+3.3 V, +5 V, +10 V, +12 V, −12 V) that power various components within circuit means 200 including components of pulser 220 and receiver 240 sections, respectively. Regulator further provides voltages to Net Burner Interface 260. The DC-to-DC converter converts low DC voltages (e.g., +5 V) to lower and/or higher voltages (e.g., +12 V and −12 V).

Inspection modalities for discriminating between various materials and fluids will now be described.

Inspection Modes

"Pulse-Echo" and "Pitch-Catch"

The inspection apparatus employs two principal inspection modalities: "pitch-catch" and "pulse-echo". The term "pitch-catch" (through-transmission) refers to a process whereby an excitation pulse or waveform is transmitted ("pitched") by a first transducer into a container, material, or fluid and received by a second transducer through a container, material, or fluid. One or more transducers are then configured to receive reflected echo pulses or waveforms (e.g., in "pulse-echo" mode). The term "pulse-echo" refers to a process whereby a transducer (e.g., a transmitting transducer) effects transmission of an acoustic pulse or waveform and one or more transducers receives the transmitted and/or reflected pulses or waveforms (echoes). Various operational configurations are possible. In one embodiment, a transmitting transducer both sends ("pitches") and receives all acoustic "echo" pulses or waveforms. In another embodiment, a first of at least two transducers receives an excitation pulse or waveform and all 1·n (odd) echo pulse(s) or waveform(s) (where n=3, 5, 7 . . . ) and a second of at least two transducers receives all 2·n (even) echo pulse(s) or waveform(s) (where n=1, 2, 3 . . . ). In another embodiment, a transmitting transducer transmits pulses or waveforms and is also configured to receive all echo pulses. In another embodiment, a first transducer transmits and receives an excitation pulse or waveform and further receives all echo pulses or waveforms. In another embodiment, a receiving transducer is used to receive both the transmitted pulse and all echo pulses. In yet other embodiments, both transmitting and receiving transducers independently receive waveforms permitting comparison of both P/E and P/C data. No limitations are intended. In yet another embodiment, one transducer transmits a pulse or waveform and a second transducer receives both the transmitted pulse and all echo pulses or waveforms (in pulse-echo mode). In yet other embodiments, both a transmitting and a receiving transducer independently receive echo pulses permitting cross-correlation of transmission and echo pulse data. In another embodiment, a transmitting transducer both sends and receives pulses or waveforms. No limitations are intended. All operational modes and transducer configurations as will be understood and implemented by those of skill in the art are encompassed hereby.

The two inspection modes (P/C and P/E) of the instant invention provide: 1) increased accuracy of wave speed and attenuation measurements, and 2) measurement redundancy for more confidence in measurements. Wave speed and attenuation measurements can be obtained from both inspection modes and exhibit close agreement. In P/C mode, the excitation waveform travels through container, material, or fluid medium one less time than is required for in P/E mode, providing for enhanced measurement vis-à-vis commercial systems known in the art. In addition, use of pulse-compression in the excitation waveform in conjunction with the P/E operational mode provides data for identifying and/or correcting for container wall thickness (e.g., providing container independent content measurements). With known (or computed) values for container wall thickness combined with data from the P/C configuration provides for precise measurement of wave speed. Further, information provided from both P/C and P/E operational modes provide container wall attenuation information, allowing for accurate acoustic attenuation measurements.

Using both pitch-catch and pulse-echo inspection modalities, acoustic pulses (0.1 to 10 MHz) are transmitted (pitched) through a container, a material (e.g., a bulk-solid material), or fluid whereby return echoes received (in pulse-echo mode) are analyzed in terms of time-of-flight and frequency content as a function of temperature to extract desired acoustic wave speed and relative attenuation data of the material or fluid being inspected. These measured values are then compared to an expandable database that includes acoustic wave speed and attenuation data for various materials and fluids whereby the wave speed and attenuation signature data permits identification of a material or fluid, e.g., inside a sealed container. Circuit means 200 in conjunction with computing means performs automated analysis of the return echoes providing results in 3-5 seconds.

Pulse Compression

The invention employs pulse compression waveforms for inspection of a container, material, or fluid. Pulse-compression is a signal processing technique that uses encoded excitation pulses or waveforms that vary in frequency as a function of time, e.g., in a linear time scale. The excitation waveform is a broadband pulse compression waveform transmitted through a container, material, or fluid being inspected permitting wave speed and relative attenuation of the propagating sound wave to be determined. Pulse compression transmits a small amplitude waveform over a long period of time without sacrificing temporal resolution. By using cross-correlation of the transmitted waveform with the received waveform, the long-duration, low amplitude waveform may be represented by a short-duration, high amplitude pulse. Effectively, the cross correlation output will appear as a broadband pulse with a width inversely proportional to the bandwidth of the transmitted chirp. The energy associated with the compressed cross-correlation pulse is directly related to the duration and bandwidth of the transmitted chirp pulse. The short-duration, high amplitude pulse retains all identifying elements of the transmitted waveform including, e.g., timing and frequency with sufficient energy for an accurate determination of wave speed and attenuation therefrom. A longer duration pulse is employed in order to achieve higher signal-to-noise ratios. In this manner, pulse compression provides the ability to detect and locate signals in the received waveforms with signal-to-noise ratios of less than 1.0 (signal amplitude is below noise amplitude). Accurate time-of-flight measurements are directly related to the frequency bandwidth of the transmitted and received pulses. Specifically, a larger bandwidth results in a greater time-of-flight resolution. Another advantage of the pulse compression technique is the ability to "deconvolve" (deconvolute) overlapping waveforms. The term "deconvolve" or "deconvolution" or "deconvolute" as the terms are used herein refer to the ability to resolve and discriminate between the various echoes within a waveform. For example, pulse compression permits resolution of closely-spaced return echoes from various reflection sources with high accuracy.

Container wall thickness can also greatly influence the accuracy of wave speed measurement through a container, material, or fluid. For example, with smaller containers filled with a fluid, the ratio of the wall thickness to fluid path begins to increase, which can cause significant errors in wave speed measurement. Thicker walls, e.g., are often found in wine bottles and test tubes. The pulse-compression technology used in conjunction with the invention provides accurate wall thickness data and in turn effectively compensates for thicker container walls, thereby increasing the accuracy of the measurement. Accurate wave speed measurements also require accurate measurements of the time of flight through the path length, which are more readily attainable at higher frequencies. For smaller containers, higher frequencies are preferred thereby achieving a much higher resolution in time measurement. For larger containers, lower frequencies are preferred. Pulse-compression provides sufficiently high signal-to-noise ratios to accurately measure the wave speed.

Excitation/Transmission Waveforms

The excitation (transmission) waveform is a modified Hanning window amplitude modulated chirp, C(t), given by Equation [8], that is optimized for a transmitting transducer 12:

$$C(t) = H(y)\sin\left(\omega_s t + \left(\frac{\pi B}{T}\right)t^2\right) \quad 0 \le t \le T \quad [8]$$

where H(t) is the Hanning window function, $\omega_s$ is the starting radial frequency, T is the pulse duration, B is the bandwidth (Hz), and t is time. The Hanning window function is determined from equation [9]:

$$H(t) = \frac{1}{2}\left[1 - \cos\left(\frac{2\pi t}{T}\right)\right] \quad [9]$$

The pulse amplitude is further modified to include a portion of the transmitted waveform at full amplitude, with both a period of "ramp up" and a period of "ramp down" at the beginning and end of the waveform, respectively. The Hanning function, H(t), is altered based on the time and the percentage, P, of the waveform at full amplitude, as denoted by the equations in [10]:

$$H(t) = \frac{1}{2}\left[1 - \cos\left(\frac{2\pi t}{T(1-P)}\right)\right] \quad 0 \le t \le \frac{T(1-P)}{2} \quad [10]$$

$$H(t) = 1 \quad \frac{T(1-P)}{2} \le t \le \frac{T(1+P)}{2}$$

$$H(t) = \frac{1}{2}\left[1 - \cos\left(\frac{2\pi(t-TP)}{T(1-P)}\right)\right] \quad \frac{T(1+P)}{2} \le t \le T$$

Figure 6:
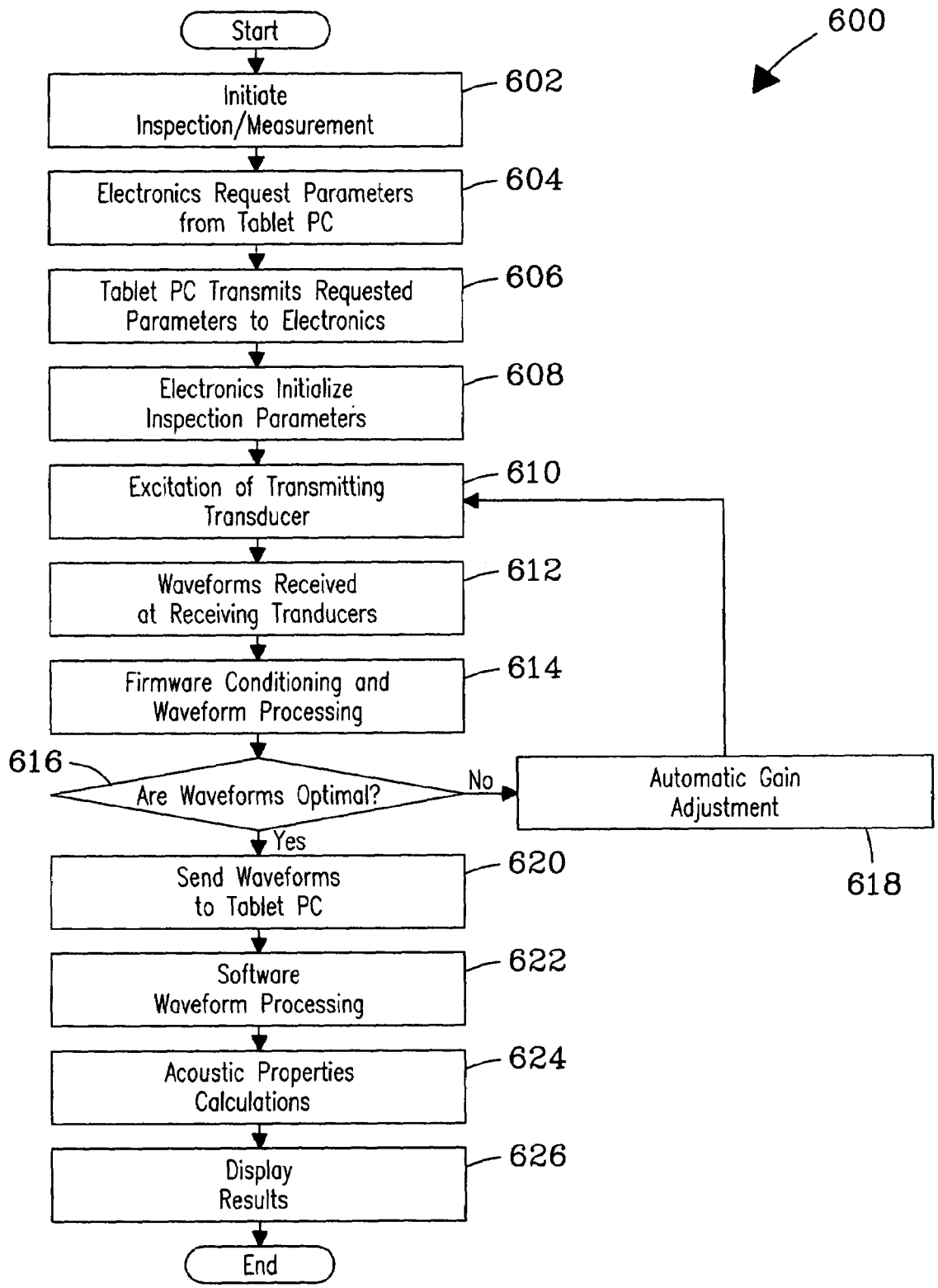
FIG. 6 illustrates a processing sequence undertaken by the inspection apparatus during an inspection of a container, material, or fluid, according to another embodiment of the process of the invention.

In one embodiment, the excitation waveform (chirp) in the inspection apparatus comprises a linear frequency sweep with 90% of the waveform at full amplitude, as illustrated in FIG. 6 (described further below), but is not limited thereto. Excitation frequency extends from about 0 MHz to about 10 MHz, but again is not limited thereto. The amplitude-modulated excitation waveform allows more energy to be transmitted into a container, material, or fluid being inspected while minimizing the large transient "start and stop" pulses associated with non-amplitude modulated waveforms.

The excitation or transmission waveform is comprised of a long-duration, broadband "chirp" encoded with a predetermined sequence or pattern involving one or more parameters selected from frequency, frequency range, time duration, rate of change of frequency with respect to time, or the like, or combinations thereof. For example, the frequency of the excitation or transmission waveform can be swept, e.g., modulated with time-dependent frequency changes. The selected encoding defines the sequence or pattern that, after appropriate filtering, is recognized in any received waveform. For example, encoding results in a compressed cross correlation function having multiple narrow-width pulses, which allows multiple echoes to be easily resolved.

In one embodiment, the encoded waveform is a time-dependent, linearly varying, frequency swept chirp (waveform), e.g., 3-V chirp or a 7-V chirp, having a specific time duration (e.g., a long-duration frequency sweep), and a specific frequency range. Thus, for example, amplitude may be ramped initially, transmitted, and then undergo a linear diminution as the pulse width nears an end while the frequency varies linearly from the beginning to end of the waveform. Lower ultrasonic frequencies allow for increased penetration, e.g., for highly attenuative materials, while higher frequencies provide increased resolution and greater measurement sensitivity, e.g., for less attenuative materials. The dry-coupling configuration allows the sensors to be employed without use of an acoustic wetting agent, or a gel or water coupling agent.

The pulse compression algorithm analyzes waveforms to determine a signal baseline and echo threshold levels, described in more detail hereafter.

Method for Inspecting a Container, Fluid, or Material for (Container-Compensated) ID of a Material or Fluid With the foregoing being given, general steps taken by a operator/user for inspecting a material, fluid, or container with inspection apparatus 100 will now be described further with reference to FIGS. 4a-4b, FIG. 5, and FIG. 6.

Figure 4A:
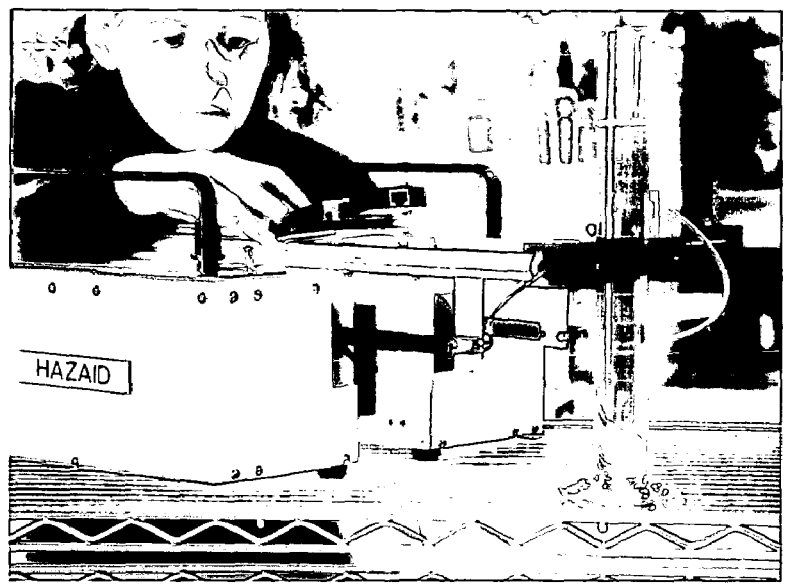
FIGS. 4a-4b illustrate inspection of large and small containers, according to two embodiments of the process of the invention.
Figure 4B:
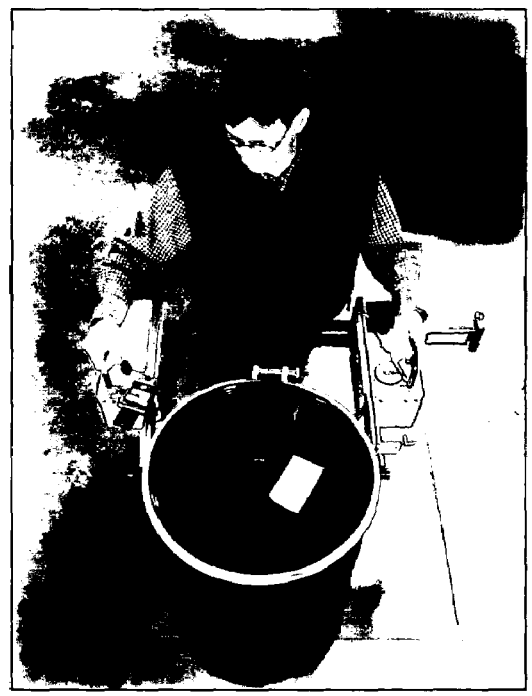

FIGS. 4a and 4b show a large and small container being inspected, respectively in conjunction with the inspection apparatus 100 of the invention, according to two embodiments of the process of the invention. In FIG. 4a, a small glass container is shown being inspected for identification of the fluid therein. In FIG. 4b, a 55-gallon drum is shown being inspected for identification of the contents therein, whether material or fluid. As observed in the figures, transducers are arranged in a configuration to allow for both pitch/catch (P/C) and pulse/echo (P/E) inspection modalities, as described herein. Use of both measurement modalities in combination allows for detailed waveform processing and analysis for identification of materials and fluids in a container.

Figure 5:
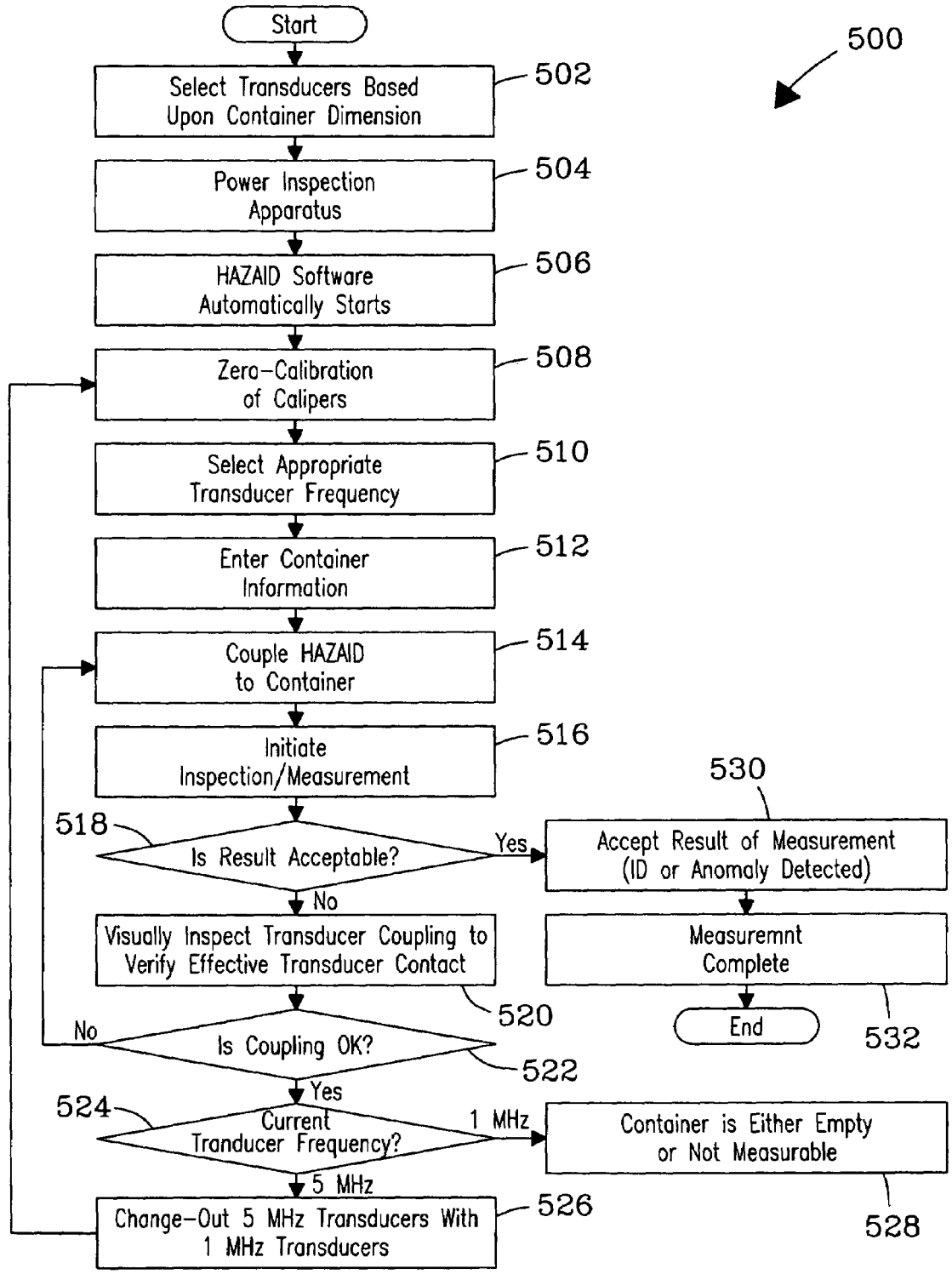
FIG. 5 illustrates a sequence for inspecting a container, according to an embodiment of the process of the invention.

FIG. 5 illustrates a sequence 500 comprising generalized steps for inspecting a container, according to an embodiment of the process of the invention. First (step 502), a user/operator of apparatus 100 selects transducers 12 (e.g., whether of a low frequency for large containers or a high frequency for small containers) based upon container dimensions. Next, at step 504, apparatus 100 is powered whereby electronic circuitry of circuit means 200 of apparatus 100 is readied for use. At step 506, software, firmware, and/or associated components are prepared for use in the instrument. Then at step 508, distance determining means 45 (e.g., calipers) are zeroed. Then, at step 510, a user may optionally select or key in a transducer frequency. Alternatively, frequency can be automatically established by the inspection apparatus based on type of transducer. Next, at step 512, information regarding the container to be inspected is selected from a list of choices by a user/operator, e.g., regarding geometry (e.g., whether flat, round, or curved), the container wall material (e.g., steel, aluminum, plastic/HDPE, glass, or ceramic). Then (step 514) transducers are coupled to the container being inspected. Next (step 516) inspection of the container is initiated. Next (step 518), the user determines if the inspection/measurement or identification of material or fluid in the container is acceptable, based on pre-defined or user-defined acceptance criteria. If results are not acceptable, at step 520, coupling of the transducers to the container can be verified. If coupling is found acceptable (step 522), but measurement remains unacceptable, selection of the transducer frequency is evaluated (step 524). If the currently selected transducer is of a high-frequency (e.g., 5 MHz), it can be exchanged (step 526) with a transducer of a low-frequency (e.g., 1 MHz). Inspection/measurement is then repeated (beginning at step 508). If the transducer currently selected is of a low-frequency, the container is empty or not measurable and should be further investigated (step 528). Alternatively, if the measurement result is acceptable by the user, identification of a material or fluid (or detection of an anomaly) is accepted (step 530) and inspection is complete (step 532).

FIG. 6 illustrates a sequence 600 comprising generalized steps undertaken by inspection apparatus 100 during an inspection/measurement of a a container, according to an embodiment of the process of the invention. First (step 602), when trigger 24 of the inspection apparatus is activated by an user/operator, the inspection/measurement is initiated. Next (step 604), parameters input by a user are requested (e.g., by circuit means 200 from computing means 40). Next (step 606), parameters are transmitted (e.g., by computing means to circuit means). Inspection parameters are then initialized including, e.g., sampling rate, initial gain settings, and other user-defined parameters (step 608). Transmitting transducer 216 is then activated and the transmission pulse is transmitted through a container, material, or fluid being inspected (step 610). Then (step 612), the transmitted waveform and any echoes are received (in either pitch-catch (P/C) or pulse-echo (P/E) mode) by receiving transducers 222. Then (step 614), received waveforms are conditioned and processed (e.g., as described in reference to FIG. 2 herein). Next (step 616), waveform amplitude is evaluated. If waveforms are not optimal (step 618), gain to the inspection apparatus is automatically adjusted (e.g., by gain component 230 of receiver circuit 240) and the transmitting transducer 216 is again activated (beginning at step 610). If optimal, waveforms are sent to computing means 40 (step 620). Computing means 40 then processes/analyzes the received waveforms (step 622). Next, acoustic wave speed and relative attenuation coefficient are calculated (step 624). Results (e.g., identification of the liquid or material, detection of an anomaly, error messages, or no material or fluid detected) are then displayed to the user and inspection/measurement ends (step 626) and inspection ends.

Algorithms

Computing means 40 provides analysis of waveform data and calculates, e.g., acoustic wave speed and attenuation of a material or fluid being inspected as a function of temperature. Computing means deconvolutes and cross-correlates waveforms and compares resultant signatures for wave speed and attenuation to a database of reference data for identifying a material or fluid being inspected. Algorithms employed by inspection apparatus 100 will now be described further hereafter.

Principle algorithms used in conjunction with the invention include, but are not limited to the following: (i) cross-correlation (deconvolution), (ii) wave speed (time-of-flight, TOF), and (iii) attenuation coefficient. Algorithms can be implemented in various ways, including, but not limited to, e.g., software, firmware, or hardware.

(i) Cross-Correlation (Deconvolution) for Time-of-Flight Determination

Figure 7:
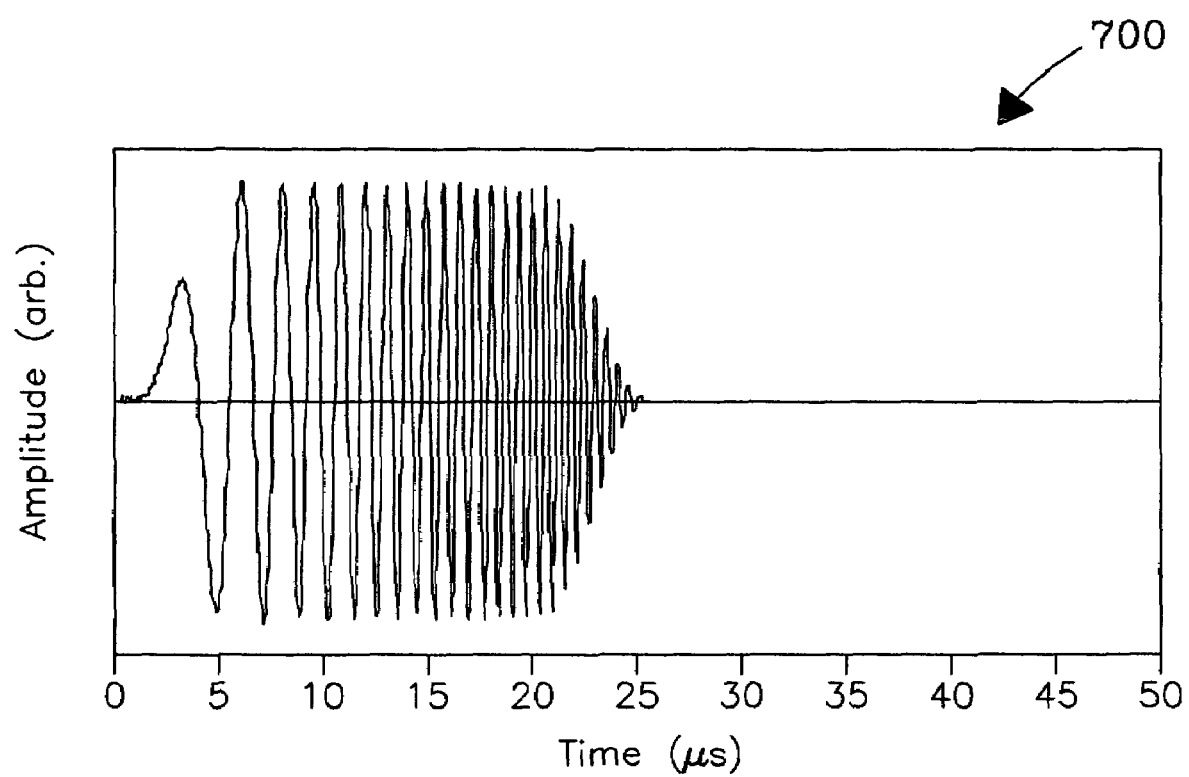
FIG. 7 illustrates a pulse-compression (encoded) waveform ("chirp") transmitted through a container or material used for inspection of the same, according to another aspect of the invention.

FIG. 7 illustrates a pulse-compression waveform ("chirp") 700 of a broadband (wide-band), and/or frequency-modulated type encoded as a function of amplitude and time (in the time domain). The "chirp" is transmitted by a transmitting transducer 12 through the container, material, or fluid being inspected. In one embodiment, the chirp is a 50 microsecond or 10 microsecond duration waveform with a linearly varying frequency of from 0 to 2 MHz or from 0 to 10 MHz for use of 1 MHz or 5 MHz transducers, respectively. The custom chirp is cross-correlated with received waveforms from both P/C and P/E inspection modalities. The term "cross-correlation" as used herein refers to the process whereby a received waveform is matched with a well-characterized transmission waveform ("chirp") identifying the specific frequency pattern within the received waveform best matching the transmission waveform for accurate determination of time-of-flight, wave speed, acoustic attenuation and/or other associated param eters. Cross correlation is effected, e.g., using a cross-correlation function, $R_{xy}(t)$, as given by Equation 11:

$$R_{xy}(t) = x(t) \otimes y(t) = \int_{-\infty}^{\infty} x(\tau) y(t + \tau) d\tau \quad [11]$$

where x(t) corresponds to the excitation waveform (signal), y(t) corresponds to a received waveform (signal), (τ) is the "time delay" between the transmitted and received signals, (t) is the time, and (⊗) represents the cross-correlation function. The integral in Equation [11] is computed as a function of the change in time delay, (dτ).

Cross-correlation sequencing was tested in conjunction with custom analysis software (e.g., Labview™, National Instruments, Inc., Austin, Tex., USA). Other algorithms and mechanisms known to those of skill in the signal-processing art e.g., match-filtering, e.g., as detailed by Savitsky-Golay (*Analytical Chemistry*, 36: 1627-1639, 1964) can be used. In other approaches, waveforms can be matched (correlated), e.g., using data point summation with subsequent filtering that identifies peak (amplitude) maxima best correlating with the point summations. Other signal processing approaches include matching of Fast Fourier transforms (FFTs) in the frequency domain. No limitations are intended. All signal processing methodologies as will be contemplated by those of skill in the art are encompassed hereby.

Figure 8A:
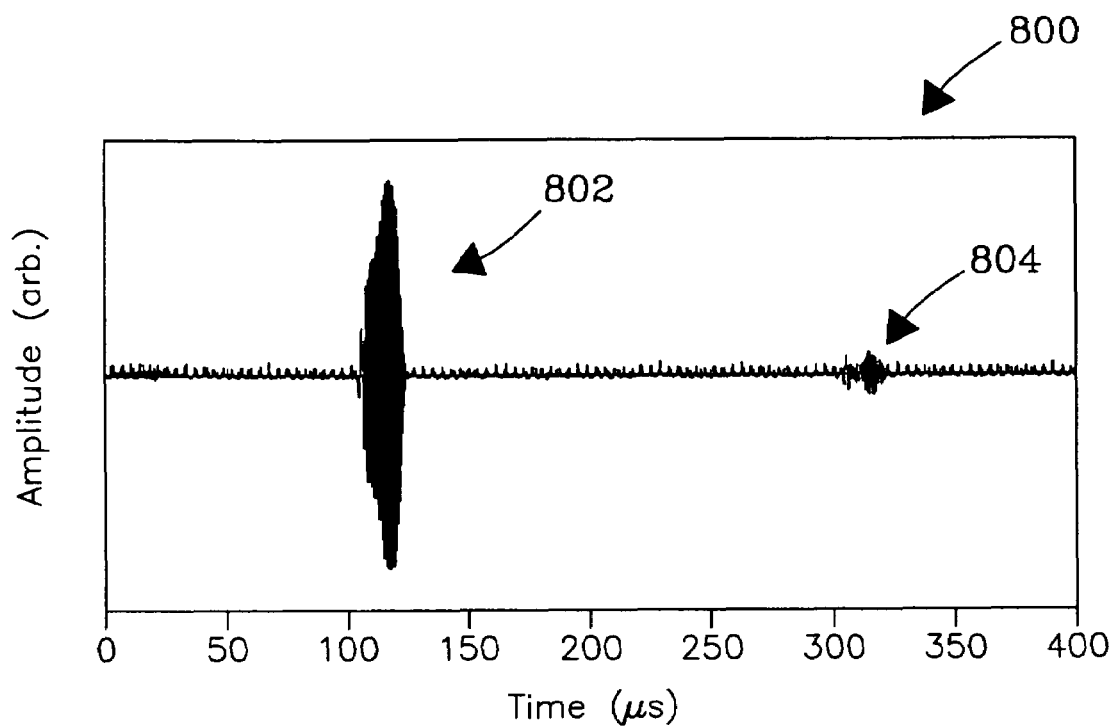
FIG. 8a illustrates a typical unprocessed (raw) waveform received by a transducer in pitch/catch mode through a container or material, according to another aspect of the process of the invention.
Figure 8B:
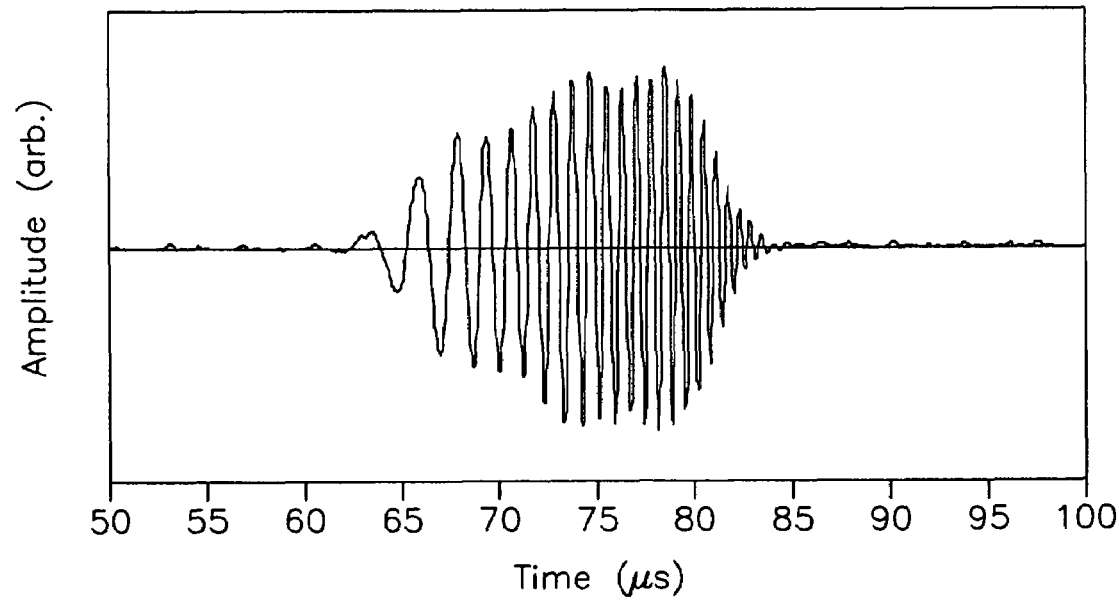
FIG. 8b shows a first pulse of FIG. 8a for cross-correlating with the transmission waveform in determination of time-of-flight, according to another aspect of the process of the invention.

FIG. 8a is a plot of amplitude vs. time showing a typical raw (unprocessed) waveform 800 received through a container, material, or fluid by a receiving transducer, according to an aspect of the process of the invention. In the figure, two pulses in waveform 800 are observed, the first pulse 802 received in pitch-catch (P/C) mode and the second pulse 804 received in pulse-echo (P/E) mode. FIG. 8b shows the first pulse 802 from FIG. 8a expanded in the time domain. Pulse 802 results from the direct transmission of the excitation waveform through a container, material, or fluid as received by the receiving transducer. Thus, it is used to determine time-of-flight, described further hereafter. The received (raw) waveform is cross-correlated with the excitation waveform. Peak maxima identified in the cross correlated waveforms retain the same time, amplitude, and frequency information as that of the received waveforms permitting time-of-flight (TOF) and thus wave speed (c) of the transmission waveform to be determined. These will now be further described in reference to FIGS. 9a-9b, FIGS. 10a-10b, and FIGS. 11a-11b.

Figure 9A:
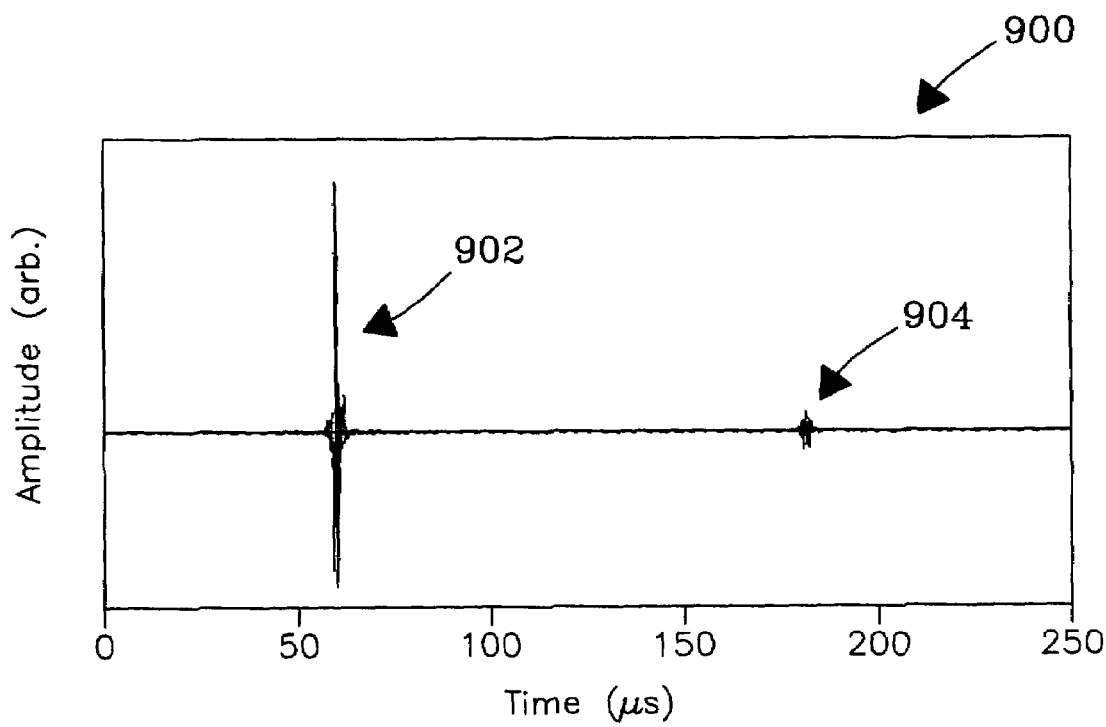
FIG. 9a is a plot of a cross-correlation waveform showing first and second pulses resulting from cross-correlation of the received (raw) waveform with an excitation ("chirp") waveform in the time domain, according to an aspect of the process of the invention.
Figure 9B:
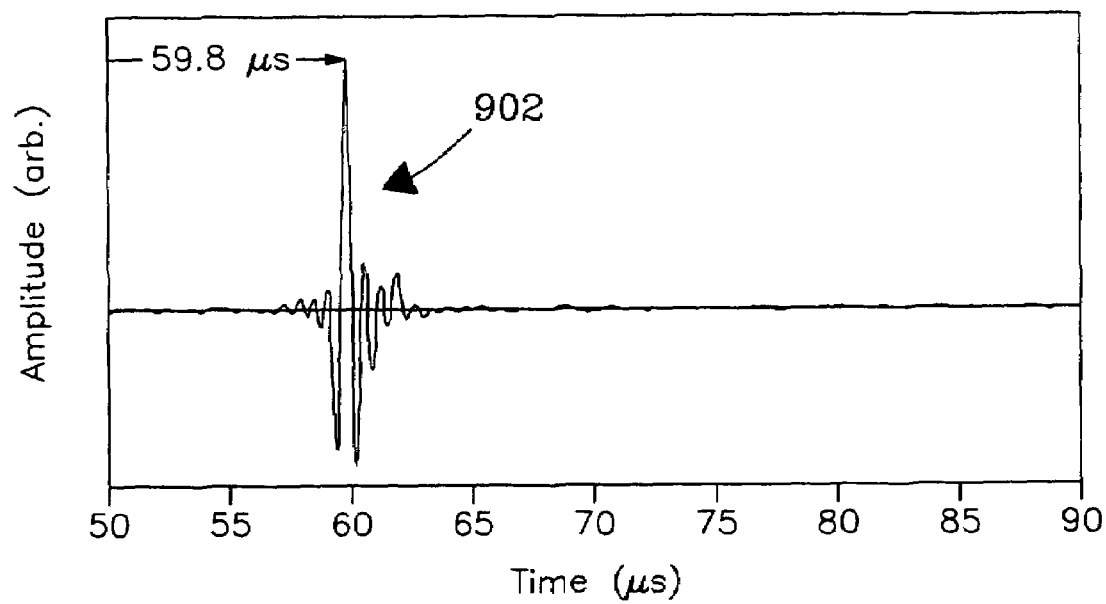
FIG. 9b is a plot of the first cross-correlation pulse of FIG. 9a expanded in the time domain providing for determination of the time-of-flight, according to another aspect of the process of the invention.

FIG. 9a is a cross-correlation waveform 900 showing first 902 and second 904 pulses resulting from cross-correlation of a received (raw) waveform with an excitation ("chirp") waveform in the time domain, according to an aspect of the process of the invention. FIG. 9b shows a first cross-correlation pulse 902 of FIG. 9a expanded in the time domain. As shown in the figure, pulse 902 correlates with the transit time of the excitation waveform through the container; thus, its peak maximum permits time-of-flight of the excitation waveform to be determined by the inspection apparatus. In the illustrative figure, TOF is determined to be 59.8 µs, but is not intended to be limiting.

Figure 10A:
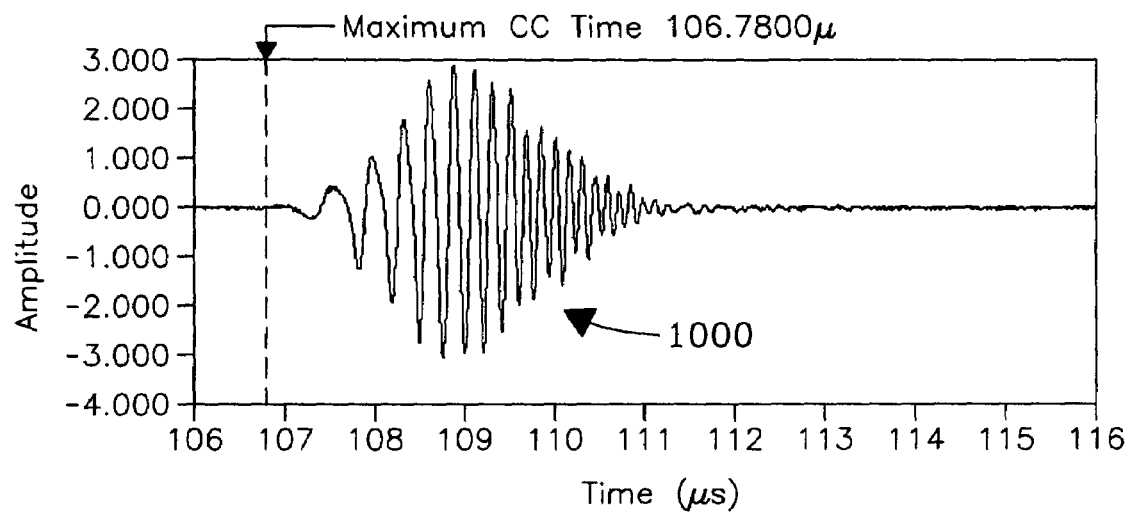
FIGS. 10a-10b present a side-by-side comparison in the same time domain of a) a raw waveform received in P/C mode and b) a corresponding cross-correlation pulse used for determination of time-of-flight, according to a further aspect of the process of the invention.
Figure 10B:
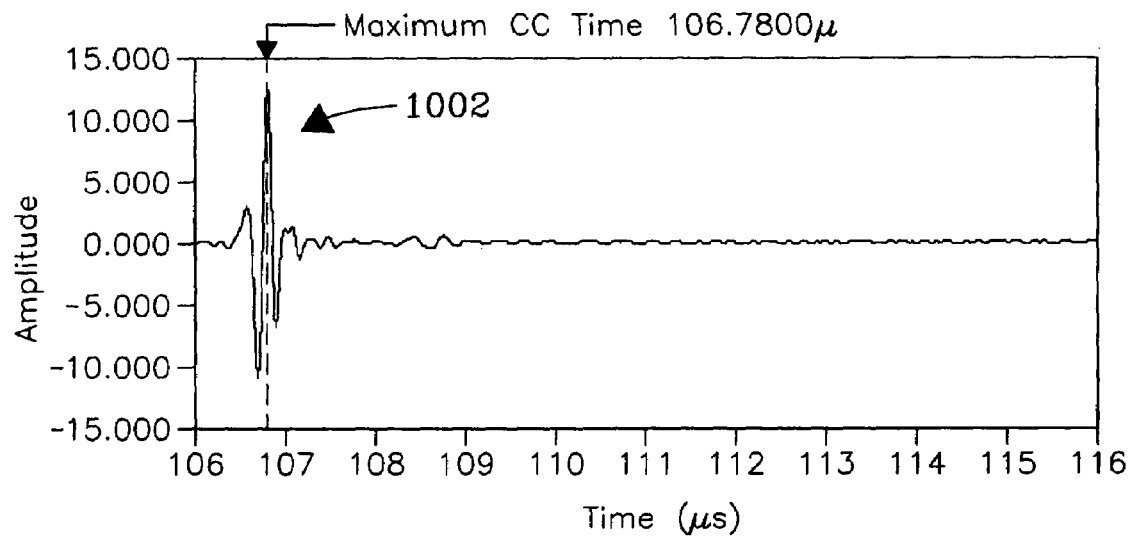

FIGS. 10a-10b present a side-by-side comparison in the same time domain of a raw waveform 1000 (FIG. 10a) received in P/C mode to its cross-correlation pulse 1002 (FIG. 10b), as may be viewed through the user interface of computing means 40, according to an embodiment of the process of the invention. As illustrated in FIG. 10b, the cross-correlation pulse 1002 has a peak maximum that correlates again with the transit time of the transmission waveform through a container, material, or fluid permitting the time-of-flight of the transmission pulse to be determined.

Figure 11A:
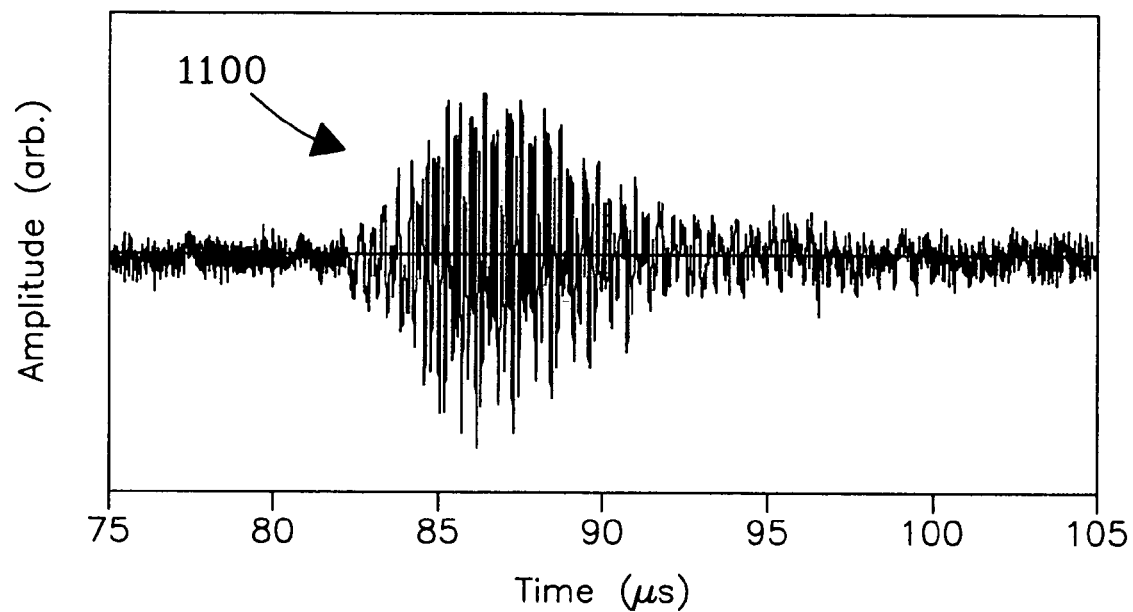
FIG. 11a illustrates a first (raw) pulse of a complex waveform received through a container in pitch-catch (P/C) mode, according to an embodiment of the process of the invention.
Figure 11B:
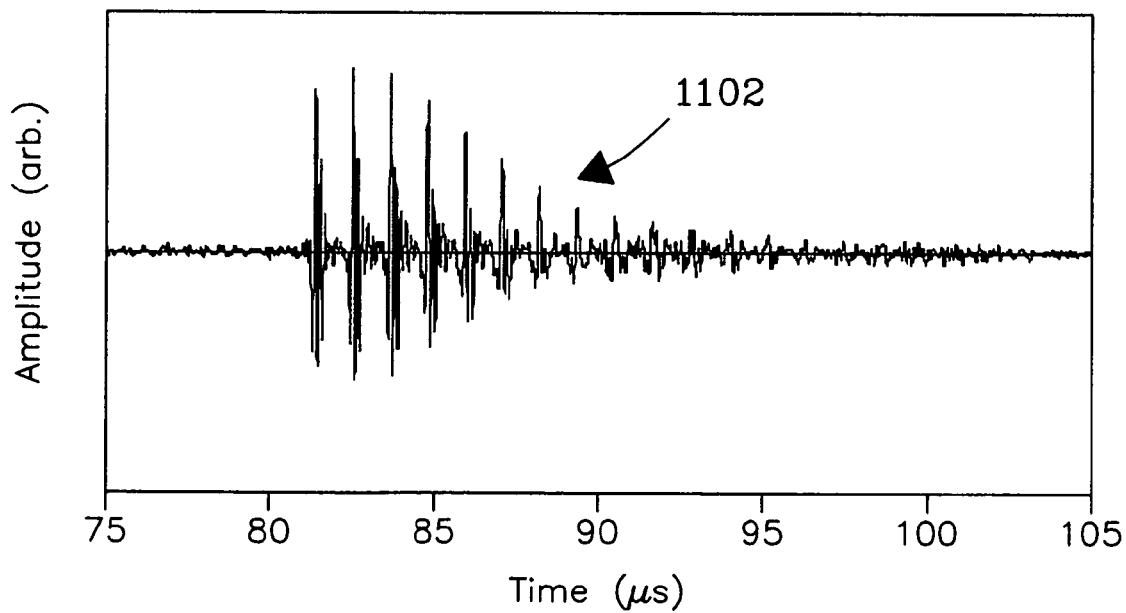
FIG. 11b illustrates cross-correlation of the waveform of FIG. 11a showing deconvolution and separation of multiple echoes in the time domain, according to an embodiment of the process of the invention.

FIG. 11a shows a first (raw) pulse 1100 of a complex waveform (not shown) received through a thick steel container in P/C mode, according to an aspect of the process of the invention. Pulse 1100 contains multiple indiscernible reflections (echos). In FIG. 11b, the corresponding cross-correlation pulse 1102 shows how cross-correlation can deconvolute and separate even complex and multiple echoes in the time domain.

Figure 12A:
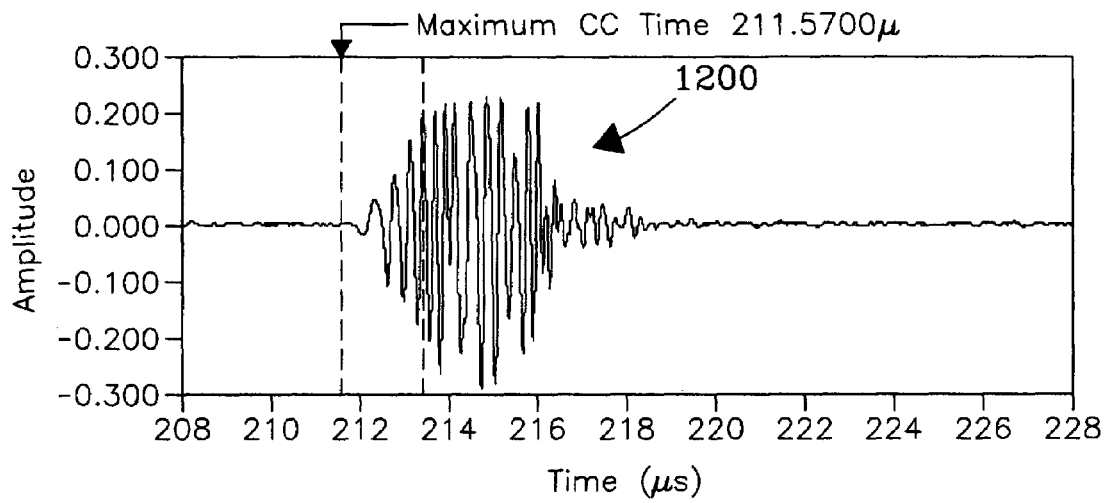
FIGS. 12a-12b present a side-by-side comparison in the same time domain of a) a complex (raw) waveform received in P/C mode and b) a corresponding cross-correlation waveform showing deconvolution and separation of two waveforms overlapping in the waveform of FIG. 12a, according to a further aspect of the process of the invention.
Figure 12B:
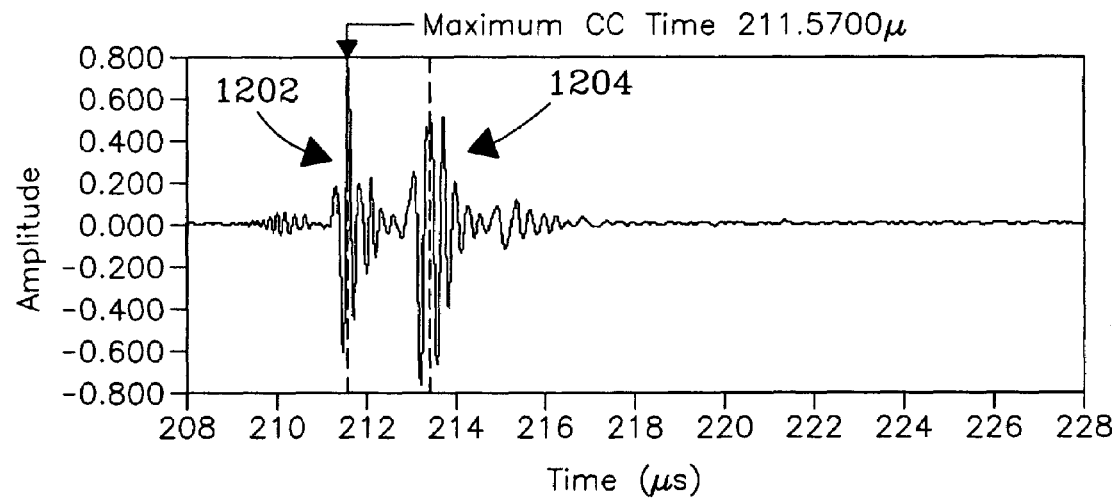

FIGS. 12a-12b present a side-by-side comparison in the same time domain of a complex (raw) waveform 1200 (consisting, e.g., of two overlapping waveforms) received in P/C mode and its corresponding cross-correlation waveform (FIG. 12b) as may be viewed through the user interface of computing means 40. In the figure, cross-correlation leads to deconvolution and separation of the two waveforms 1202 and 1204 overlapping previously in waveform 1200 (FIG. 12a). As illustrated in FIG. 12b, the cross-correlation waveforms 1202 and 1204 have peak maxima that correlate again with the transit time of their respective transmission waveforms through a container, material, or fluid permitting their respective times-of-flight to be determined.

Determination of acoustic wave speed from waveform data will now be described hereafter.

(ii) Acoustic Wave speed

Figure 13:
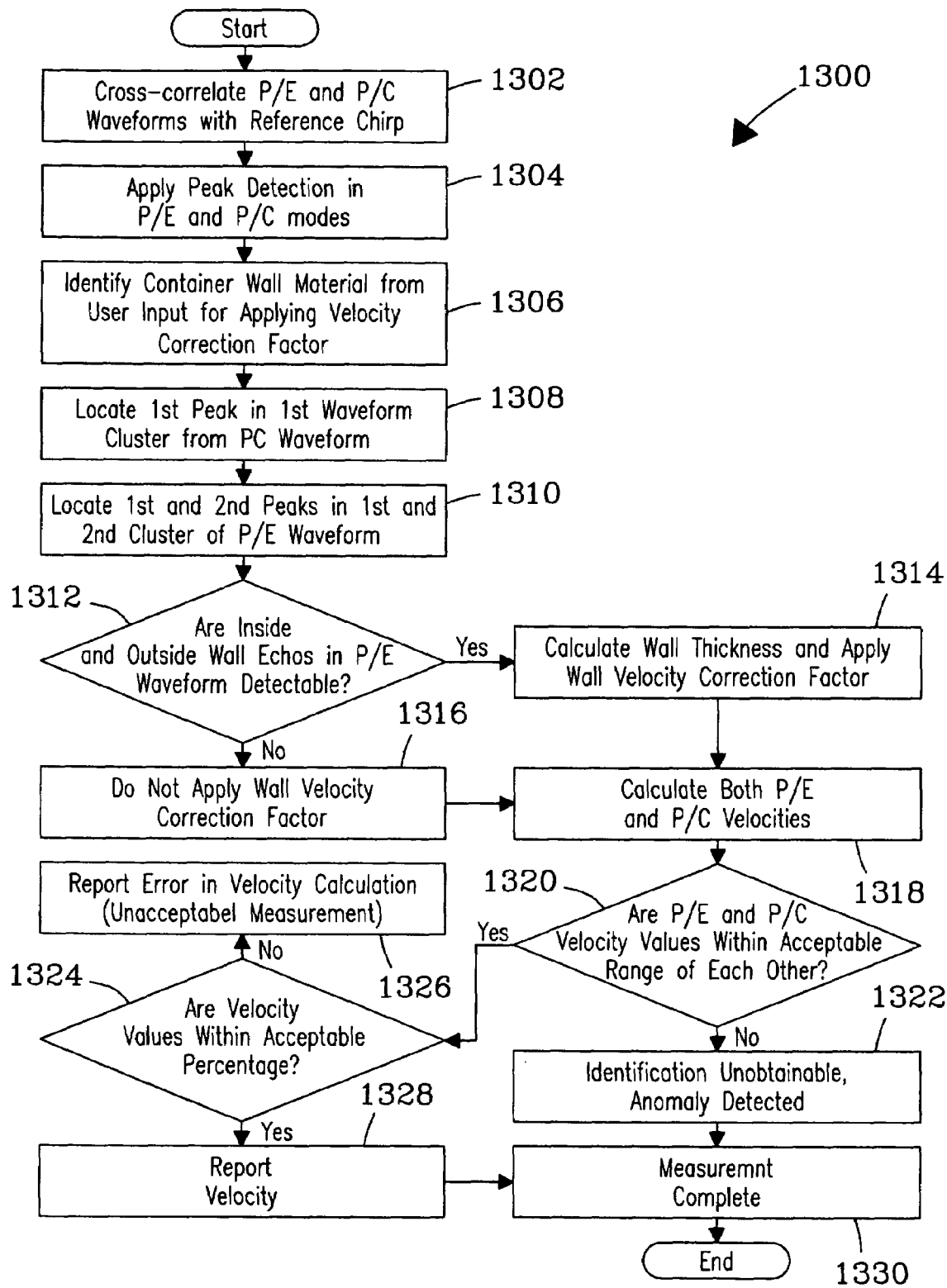
FIG. 13 illustrates a sequence for determination of acoustic wave speed in conjunction with time-of-flight values determined from cross-correlation of transmitted and received waveforms, according to an embodiment of the process of the invention.

With TOF values determined as described herein (see Deconvolution and Cross-Correlation), acoustic wave speed is subsequently calculated and displayed to an operator. Computing means 40 correlates path length or distance, time of flight of the pulses or waveforms, and temperature of the material or fluid being inspected to calculate a temperature-compensated acoustic wave speed value. FIG. 13 illustrates a general sequence 1300 for determination of acoustic wave speed in conjunction with cross-correlation of transmitted and received waveforms, according to an embodiment of the process of the invention. In the figure (at step 1302), waveforms received in Pitch-Catch (P/C) and Pulse-Echo (P/E) modes through a container, material, or fluid are cross-correlated with an excitation or transmission pulse ("chirp"). Next (step 1304), cross-correlation peaks are identified. Then (at step 1306), composition of a container wall (if available) is identified by a user/operator and a composition is selected from, e.g., a list of same through the user interface of computing means, e.g., whether steel, aluminum, plastic/HDPE, glass, ceramic, or its closest match. From these materials, inspection apparatus can optionally apply wave speed correction factors to calculations made in conjunction with cross-correlation waveforms. Next (step 1308), a first peak (maximum) in a first (P/C) cross-correlation waveform or cluster of waveforms is located and a TOF determined, as described herein, e.g., in conjunction with e.g., $1^{st}$ and $2^{nd}$ derivatives, deconvolution, cross-correlation, match-filtering, Savitsky-Golay method, or the like. No limitations are intended. Next (at step 1310), if pulse echoes representative of inside wall and outside container wall reflections (echoes) are identifiable in the cross correlation waveform (e.g., in a first cluster of a P/E waveform), first and second peak maxima are located (e.g., using Savitsky-Golay approach described herein) and corresponding time-of-flight values are determined. Next, if first and second peak maxima are located or determined corresponding to inside and outside wall echoes (step 1312), a wall thickness can be determined and a correction factor optionally applied compensating for the container wall (at step 1314). If (at step 1316) first and second peak maxima are not located or determined, a wave speed correction factor compensating for container wall is not applied. Wave speed is then calculated from both P/E and P/C modalities (step 1318). Next (step 1320), both the P/E and P/C wave speeds are evaluated based on user-defined acceptance criteria or metrics (e.g., are the acoustic wave speeds from P/E vs P/C values within 10% of each other or acceptable?). If not acceptable, identification of the material or fluid is not determined or an "anomaly detected" warning is displayed (step 1322). Optionally or alternatively, if P/C and/or P/E wave speeds meet the initial acceptance criteria, a more rigorous user-defined acceptance assessment can be made (e.g., are the acoustic wave speeds from P/E and P/C calculations within 2% of each other?) (step 1324). If user-defined or established criteria are not met, an "error" or "unacceptable measurement" can be displayed to the user (step 1326). Otherwise (step 1328), acoustic wave speeds can be reported to the user. Wave speed determination ends (step 1330).

Sequence steps described hereinabove for FIG. 13 encompass those described single and multiple waveforms received through a container, material, or fluid. All signal processing steps as will be contemplated by those of skill in the art are encompassed hereby. No limitations are intended.

(iii) Attenuation Coefficient

The attenuation coefficient algorithms compare pulse and/or waveform data as a function of frequency and temperature providing attenuation results as a second signature or parameter enabling a user/operator of the inspection apparatus 100 to identify and discriminate a much wider range of materials and fluids. As discussed herein, the cross-correlation function contains frequency-dependent time and amplitude information. In fact, multiple container wall reflections are easily distinguished in CC waveforms. This information allows pulses data of interest to be isolated from adjacent reflections in a waveform. Further, echoes resulting from inner and outerwall reflections of a container can be used to correct waveform data for container. Using signals from the P/C transducer, the arrival of the first and second arrival of the chirp pulse train were identified. The first and second arrivals correspond to the pulse travel having traveled through the media one and three times, respectively. Each arrival of the pulse train may be composed of multiple echoes (each corresponding to a pulse in the CC waveform) due to in-wall and/or interface reflections. By extracting the appropriate CC pulses and performing a Fast Fourier Transform (FFT), the frequency-dependent amplitude is determined. A customized analysis program written in Labview™ was used to compare the frequency spectra of the two arrivals. When divided by the appropriate distance (twice the container diameter in this case), this results in a frequency-dependent measure of attenuation. Custom software algorithms are written to perform the processing scheme used by computing means 40. The analysis program and sequencing associated with the user interface of computing means 40 was developed in conjunction with Labview™ software (National Instruments, Inc., Austin, Tex., USA), but is not limited.

Figure 14:
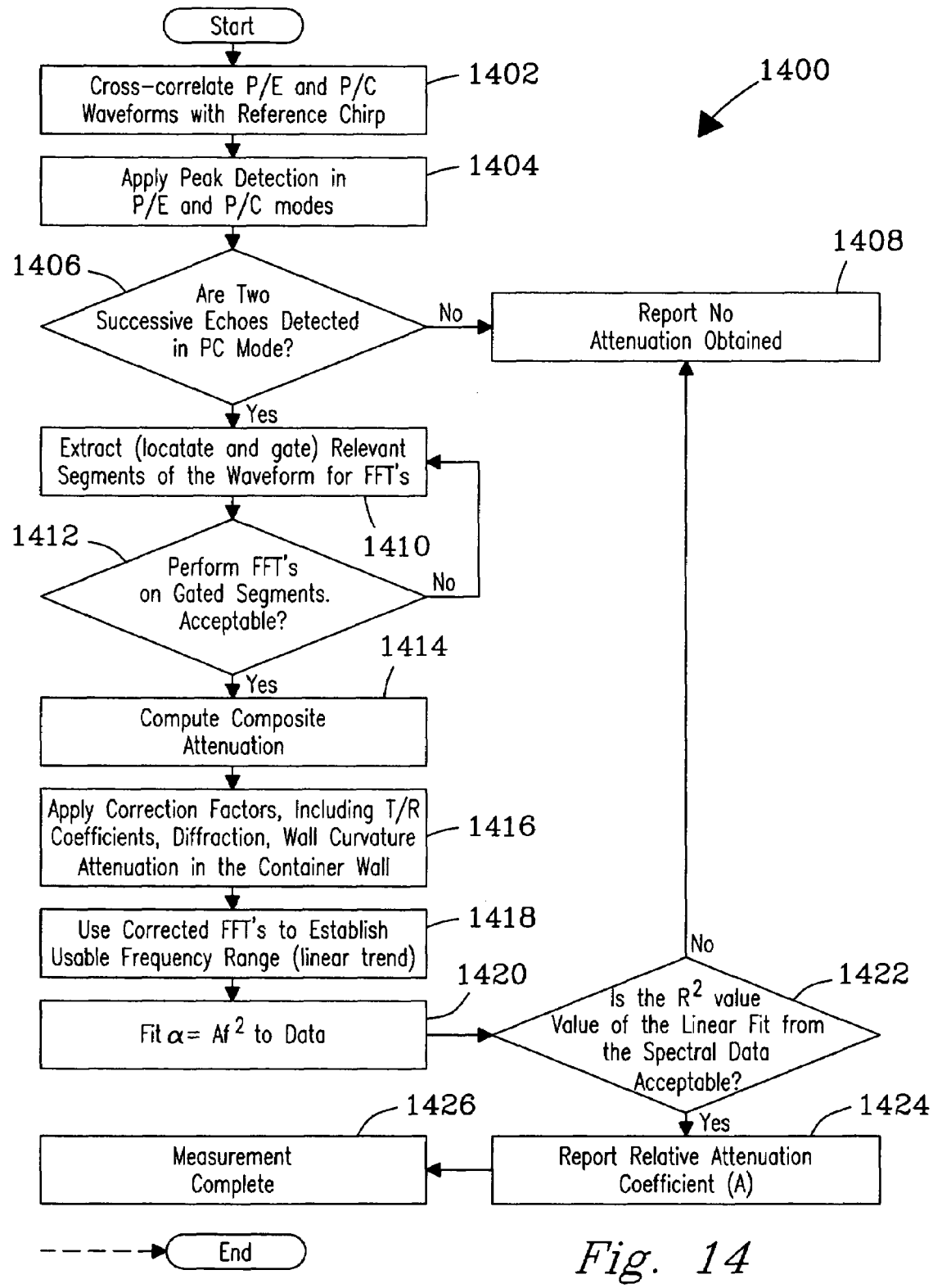
FIG. 14 illustrates a generalized sequence for determination of acoustic attenuation in conjunction with time-of-flight from cross-correlation of transmitted and received waveforms, according to an embodiment of the process of the invention.

FIG. 14 illustrates a general sequence 1400 for determination of acoustic attenuation in conjunction with cross-correlation of transmitted and received waveforms. First (at step 1402), any waveforms (i.e., from Pulse-Echo (P/E) and Pitch-Catch (P/C) mode) received through a material or fluid (e.g., in a container) are cross-correlated with a reference transmission pulse ("chirp"). Next (at step 1404), cross-correlation peaks are detected. Next (at step 1406), two successive (P/C mode) (cross-correlation) pulse echoes waveforms are searched for. If two or fewer are found, "no attenuation value obtained" is reported to the user for the inspection measurement and measurement ends (at step 1408). Alternatively, if two successive echoes are detected in the P/C waveform, pertinent segments of the waveforms are extracted, i.e., located and gated (at step 1410). The term "gated" refers to the number of sampling points selected and extracted (e.g., from 75 to 500) from any P/C or P/E waveforms for subsequent cross-correlation, Savitsky-Golay, FFT, or other calculations. As will be understood by those of skill in the art, for example, gating can comprise various sampling sizes improving data handling, signal processing, and precision and accuracy. No limitations are intended. Next (step 1412), e.g., FFTs (or other correlation algorithms) for gated segments are calculated or instituted. If the FFTs of the gated segments are not acceptable (e.g., too few data points, signal saturation determined, or other errors), steps 1410 and 1412 can be repeated iteratively. If FFTs are acceptable, a composite attenuation is calculated as a function of frequency from equation [6] (step 1414). Next (step 1416), any known correction factors including, but not limited to, e.g., transmission/reflection coefficients, corrections for diffraction, dispersion, relaxation, etc., wall curvature factors (e.g., whether flat, round, or curved), and/or attenuation factors based on composition of the container wall (e.g., whether steel, aluminum, plastic/HDPE, glass, or ceramic), or the like based on user input or other data are applied. From the corrected FFTs, linear trends of useable frequency ranges are identified and/or compiled (step 1418). In one illustrative and exemplary compilation approach, for example, the maximum of the low frequency limit (−6 dB down from maximum) of a first FFT waveform and the minimum of the high frequency limit (−6 dB down from maximum) of a second FFT waveform establish the inclusion area for the selected frequencies, but is not limited thereto. All signal processing techniques as will be contemplated by those of skill in the art are encompassed hereby. No limitations are intended. Next (step 1420), attenuation data are plotted, e.g, as a linear function of the squared frequency and fit, e.g., using a least squares fitting algorithm (i.e., $\alpha = Af^2$, where A is the slope of the line in the fit) or other suitable fitting or regression routine and a slope or regression determined from the fit thereby determining the attenuation coefficient ($\alpha$). Next (step 1422), data are evaluated against user-defined acceptance metric (e.g., is an $R^2$ value determined from the least squares fit acceptable?). If not acceptable, a "no attenuation value obtained" is reported to the user/operator (step 1408) and attenuation determination ends. Otherwise (step 1424), relative attenuation coefficient is reported to the user/operator and attenuation determination ends (step 1426).

Figure 15A:
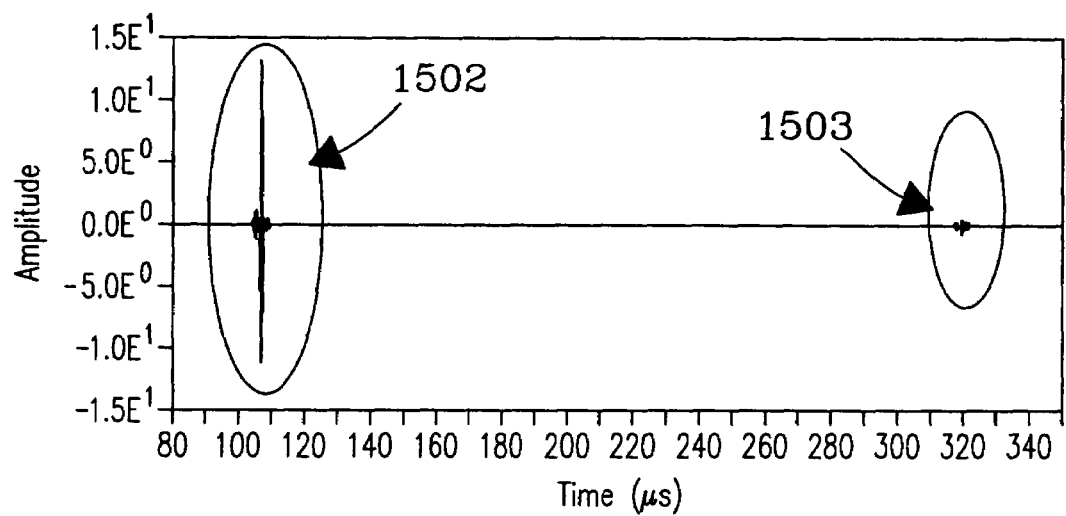
FIGS. 15a-15f illustrate graphical representations of sequence steps in FIG. 14 for determination of acoustic attenuation.
Figure 15B:
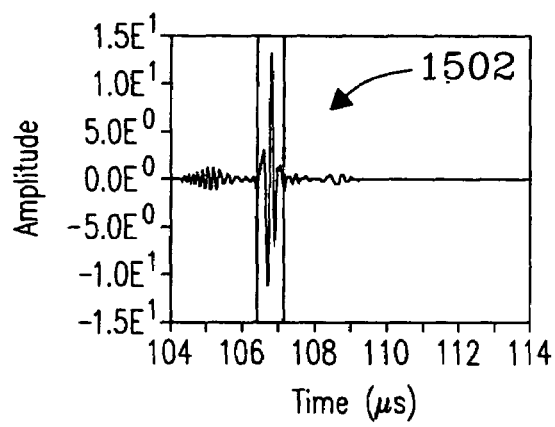
Figure 15C:
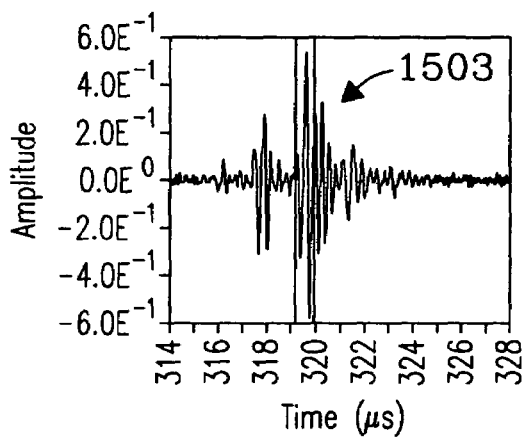
Figure 15D:
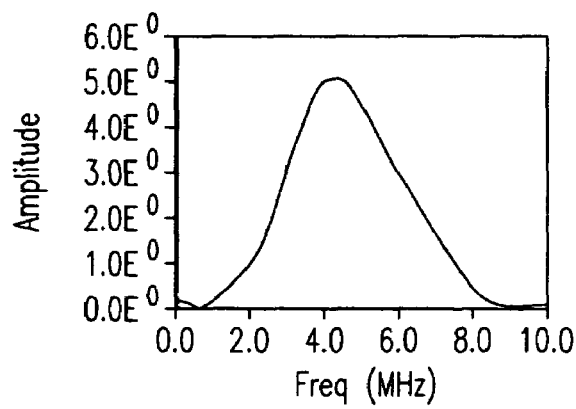
Figure 15E:
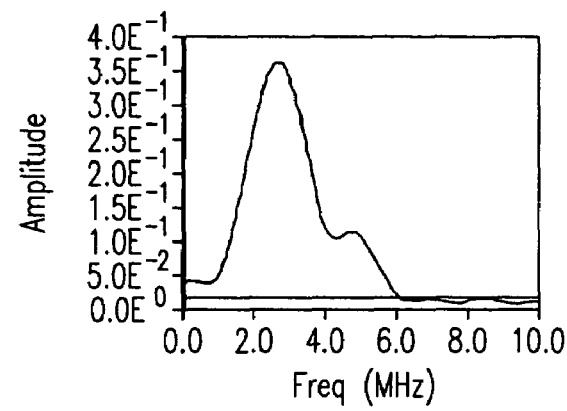
Figure 15F:
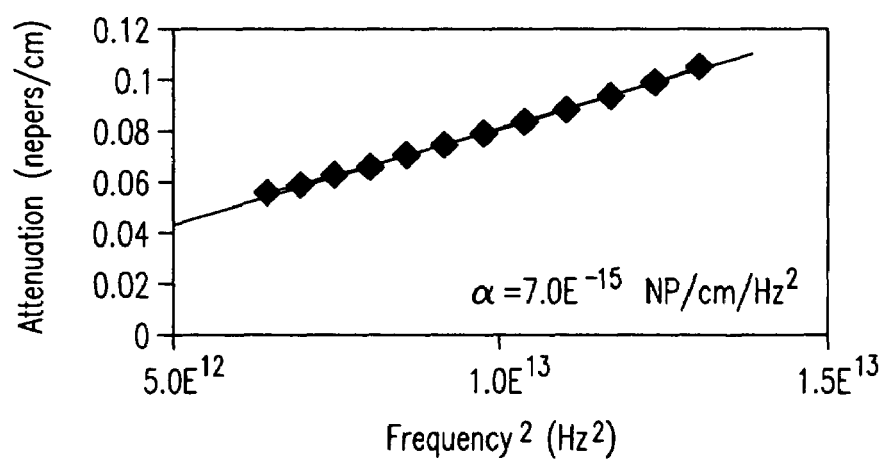

Sequence steps described hereinabove for FIG. 14 are illustrated graphically in FIGS. 15a-15f. FIG. 15a illustrates the process whereby two cross-correlated P/C reflection pulses (1502 and 1503, respectively) from a cross-correlation (CC) of received waveforms are located and selected (see steps 1402-1404, FIG. 14). FIGS. 15b-15c illustrate the process whereby (e.g., 75 or more) sample points from each reflection pulse in FIG. 15a are selected (gated) and extracted; number of points is user-defined (see steps 1406-1410, FIG. 14). FIGS. 15d-14e illustrate the process whereby Fast Fourier Transforms (FFTS) of selected gate portions in FIGS. 15b-15c are calculated, e.g., as described herein with reference to Equation [6] (see step 1412, FIG. 14) and attenuation determined. FIG. 15f illustrates the process whereby attenuation data are plotted as a function of squared frequency and fit, e.g., to a line, to determine the attenuation coefficient (see steps 1414-1420, FIG. 14). All signal processing steps as will be contemplated by those of skill in the art are encompassed hereby. No limitations are intended.

Acoustic Wave speed and Attenuation as Signatures for Material/Fluid Identification Computing means 40 correlates temperature compensated values for acoustic wave speed and attenuation providing them as unique signatures for discriminating and identifying materials and fluids. Computing means 40 has a tailored, expandable database with a listing of discrimination values as a function of temperature for various materials and fluids. Measured time-of-flight values for a given waveform are compared with similar database values containing reference information on a large number of reference waveforms. In each case, the time-of-flight reference waveforms are ascertained in the same manner as the readings being taken, thus providing for accurate matches and accurate material identification. When a match-up is found, the pertinent information is retrieved and displayed to the operator so appropriate action can be taken.

For example, if the analysis of the acoustic echo by an inspection officer in a border control application indicates that there is possibly something improper about the container or its perceived contents, the officer can impound the container. Alternatively, if no match occurs, i.e., the inspection proves negative, the officer can allow a container to pass inspection. And, within the broader scope of the present invention, the database match-up process applies equally well to interrogation of online and/or real-time monitoring of materials in flow systems (e.g., pipes, duct-work, venting, etc.) or process control stations, as well as inspection of bulk liquids, as well as solid form commodities inside or outside of sealed containers.

Figure 16A:
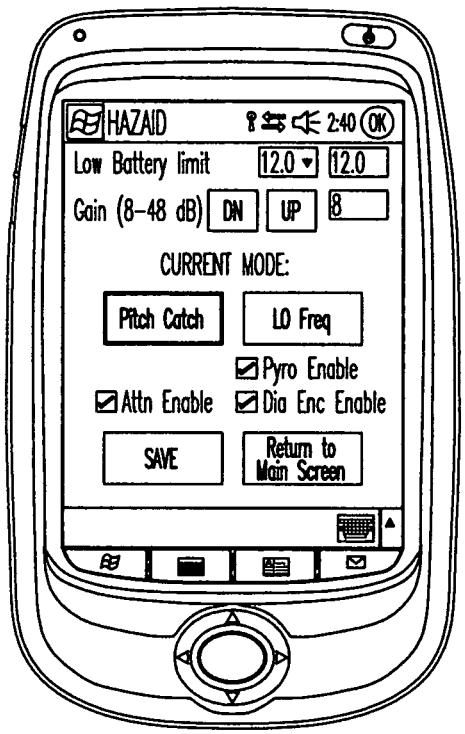
FIGS. 16a-16b shows two different views of a user interface of computing means showing a) choices of user-defined input parameters of a type available for selection by a user/operator, and b) acoustic wave speed and attenuation values determined following inspection of a container, material, or fluid indicating identification of same, according to an aspect of the apparatus of the invention.
Figure 16B:
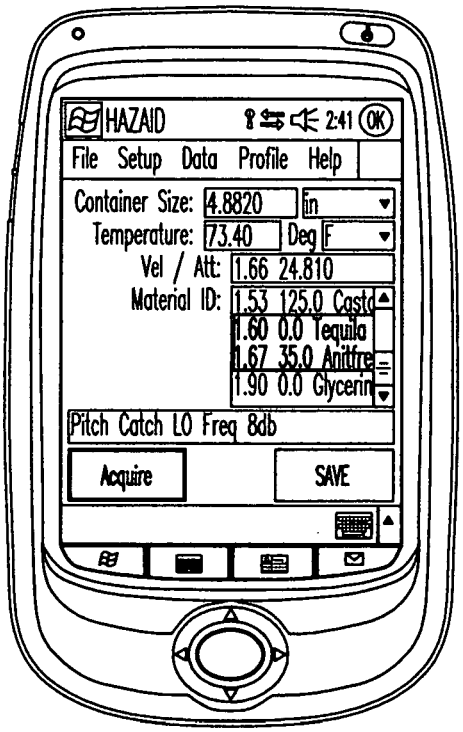

FIGS. 16a-16b present two separate views of the user interface of the computing means. In FIG. 16a, the user interface is shown displaying various input variables. Input variables include, but are not limited to, e.g., material identification (ID); check indicator (%); or how close a lookup ID must be to the measured value; Manual Gain (e.g., 8-48 dB); Automatic Gain Enable; Attenuation Enable; Operational Mode (e.g., Pitch-Catch and/or Pulse-Echo); Transducer Frequency; Gate parameters, or number of peak sampling points; Filenames, for storing inspection data and description information; mode (e.g., P/E or P/C); frequency (e.g., High or Low); Temperature Sensor Enable, Distance Measuring Enable; and other user/operator selection variables. All such variables/parameters as will be contemplated by those of skill in the art can be configured for selection through the user interface. No limitations are intended. In FIG. 16b, the user interface displays values including, but not limited to, e.g., acoustic wave speed and acoustic attenuation calculated from inspection of an unknown fluid, temperature, container size, frequency, or the like. In the instant case, acoustic wave speed is shown to be about 1.66 (Km/second). Attenuation coefficient is shown to be about 24.810 (Nepers/cm/Hz$^2$), providing a second signature for discrimination between materials and fluids having similar acoustic properties. In the figure, a highlighted list of materials and fluids having discrimination signatures closest to those calculated for the inspected material or fluid at the measured temperature are displayed to a user/operator, being identified as Antifreeze.

TABLE 2 presents a selected list of physical property data for various fluids illustrating how attenuation can vary significantly even when acoustic wave speed is similar in magnitude. Acoustic properties of a wide array of solid, liquids and gases are available, e.g., as detailed by M. W. Moyer et al. (*Table of Acoustic Velocities and Calculated Acoustic Properties for Solids, Plastics, Epoxies, Rubbers, Liquids and Gases*, Y-12 Plant, Oak Ridge National Laboratory, Tenn., USA). Also, a list of acoustic material properties can be found on the internet at http://www.ultrasonic.com/Tables/index.html.

TABLE 2

Illustrative Physical Property Data for various constituent fluids.

| Material | Viscosity (poise) | Density (API Gravity) | Surface Tension (dynes/cm) | Acoustic Wave speed (mm/usec) | Attenuation (neper/cm) X 10$^{-5}$ |
|---|---|---|---|---|---|
| Water | 0.01 | 10 | 76 | 1.5 | 25 |
| Gasoline | 0.006 | 50 to 70 | 26 | 1.4 | 31 |
| Kerosene | 2 | 40 to 50 | 30 | 1.3 | 110 |
| Lubricating Oil | 0.08 to 12.0 | 12 to 33 | 32 to 34 | 1.62 | >2000 |

In sum, the acoustic wave speed and attenuation data acquired by inspection apparatus 100 is accurate and precise in their respective methodology, and are sufficiently sensitive to consistently identify and discriminate Classic Coca Cola from Diet Coca Cola where, e.g., the difference in wave speeds between the two fluids is approximately 3%. As will be further understood by those of skill in the art, the database listing of discrimination values for identifying materials and fluids is may be expanded without limitation. Thus, no limitations are intended.

CONCLUSIONS

While the preferred embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

We claim:

1. An inspection apparatus for multiparameter acoustic inspection and identification, comprising:
   at least two transducers operably disposed for inspection of a container, a material, and/or a fluid, wherein at least one of the at least two transducers transmits an acoustic excitation pulse(s) or waveform(s) through the container, material, or fluid for inspection of same and one or more of the at least two transducers receives the pulse(s) or waveform(s) transmitted through, and/or reflected in, the container, material and/or fluid;
   dry coupling means operably disposed for coupling said at least two transducers to said container, material, and/or fluid whereby said pulse(s) or waveform(s) have sufficiently high throughput energy through said container, material, and/or fluid providing for analysis of same;
   path length measuring means operably disposed for measuring acoustic path length of said pulse(s) or waveform(s);
   temperature measuring means operably disposed for measuring temperature of said container, material, and/or fluid;
   circuit means operably disposed to said transducers for conditioning of said pulse(s) or waveform(s) transmitted and/or received through the container, material, and/or fluid;
   computing means electrically coupled to said circuit means providing for at least an analysis of said pulse(s) or waveform(s) conditioned by said circuit means; and,
   wherein analysis of said pulse(s) or waveform(s) and/or a portion thereof as a function of temperature by said inspection apparatus provides at least a first and a second acoustic discrimination signature for identifying said material and/or said fluid being inspected.

2. An apparatus of claim 1, wherein said transducers are operably disposed for contacting opposing surfaces of the container or the material for inspection of same.

3. An apparatus of claim 1, wherein said at least two transducers are in vertical and horizontal alignment to each other.

4. An apparatus of claim 1, wherein said at least two transducers include a 1 MHz transducer and a 5 MHz transducer, with operational frequencies of 0 MHz to 2 MHz or of 0 MHz to 10 MHz, respectively.

5. An apparatus of claim 1, wherein said excitation pulse(s) or waveform(s) is a wide-band, frequency-modulated pulse(s) or waveform(s).

6. An apparatus of claim 1, wherein said excitation pulse(s) or waveform(s) is an encoded chirp.

7. An apparatus of claim 6, wherein said encoding of said excitation pulse(s) or waveform(s) comprises pulse compression retaining frequency and amplitude information in received waveforms that permits deconvolution and cross-correlation of same.

8. An apparatus of claim 6, wherein said excitation pulse(s) or waveforms comprises a linear frequency sweep with 90% of the pulse or waveform at full amplitude, wherein the excitation frequency extends from about 0 MHz to about 10 MHz.

9. An apparatus of claim 1, wherein said excitation pulse(s) or waveform(s) is transmitted by a first of the at least two transducers in pitch-catch mode through said container, material, or fluid being inspected and said received pulse(s) or waveform(s) are received by at least a second of said at least two transducers in pulse-echo mode.

10. An apparatus of claim 9, wherein said first of said at least two transducers is operable for receiving all 2·n (even) echo pulse(s) (where n=1, 2, 3 . . . ) and said second of said at least two transducers is operable for receiving said excitation pulse(s) or waveform(s) and all 1·n (odd) echo pulse(s) (where n=3,5,7 . . . ).

11. An apparatus of claim 1, wherein said portion of said pulse(s) or waveform(s) is a gated portion selected from a cross correlation thereof of a selected frequency range.

12. An apparatus of claim 11, wherein said analysis of said pulse(s) or waveform(s) comprises deconvolution and a fast Fourier transform of said gated portion(s).

13. An apparatus of claim 1, wherein said analysis of said pulse(s) or waveform(s) comprises deconvolution by cross-correlation of same with said excitation pulse(s) or waveform(s) for determining acoustic wave speed as a first acoustic discrimination value and relative attenuation coefficient as a second discrimination value for identifying said material or said fluid.

14. An apparatus of claim 1, wherein said first and second acoustic discrimination signatures are acoustic wave speed and relative acoustic attenuation, respectively.

15. An apparatus of claim 1, further comprising a support means operable for extension and retraction of varying distance along a horizontal axis providing for attachment of said transducers to opposing sides of the container, or the material for inspection of same.

16. An apparatus of claim 1, wherein said temperature measuring means is an infra-red laser pyrometer operably connected to each of said at least two transducers.

17. An apparatus of claim 1, wherein said coupling means is a dry coupling means that does not require a wetting agent for contacting the container being inspected.

18. An apparatus of claim 17, wherein said dry coupling means comprises a low-attenuation elastomer.

19. An apparatus of claim 1, wherein said coupling means has an acoustic impedance substantially matching that of said container, material, or fluid being inspected for acoustically coupling said transducers thereto.

20. An apparatus of claim 1, wherein said computing means comprises a user interface for setting and/or controlling at least one of amplitude, frequency, pulse width, digitizing rate, or combinations thereof by an operator.

21. An apparatus as recited in claim 1, wherein said circuit means comprises a multiplexer comprising at least one relay and one or more Power MOSFETS for rapid switching between inspection modalities for inspection and/or operation.

22. A method for multiparameter acoustic inspection and identification, comprising the steps:
   providing an inspection apparatus comprising:
      at least two transducers operably disposed for inspection of a container, a material, and/or a fluid, at least one of the at least two transducers transmits an acoustic excitation pulse(s) or waveform(s) through the container, material, and/or fluid for inspection of same and one or more of the at least two transducers receives the pulse(s) or waveform(s) transmitted through, and/or reflected in, the container, material and/or fluid;
      dry coupling means operably disposed for coupling said transducers to said container, material, or fluid whereby said pulse(s) or waveform(s) have sufficiently high throughput energy through said container, material, and/or fluid providing for analysis of same;
      path length measuring means operably disposed for measuring acoustic path length of said pulse(s) or waveform(s);

temperature measuring means operably disposed for measuring temperature of said container, material, and/or fluid;

circuit means operably disposed to said transducers for conditioning of said pulse(s) or waveform(s) transmitted and/or received through the container, material, and/or fluid;

computing means electrically coupled to said circuit means providing for at least an analysis of said pulse(s) or waveform(s) conditioned by said circuit means; and, selecting a location for transmitting said excitation pulse(s) or waveform(s) through said container, material, and/or fluid to said one or more of the at least two transducers in a receiving location;

transmitting said excitation pulse(s) or waveform(s) into said container, material, and/or fluid being inspected;

receiving said excitation pulse(s) or waveform(s) and any reflected pulse(s) or waveform(s) through said container, material, and/or fluid;

wherein analysis of said pulse(s) or waveform(s) and/or a portion thereof as a function of temperature by said inspection apparatus provides at least a first and a second acoustic discrimination signature for identifying said material and/or said fluid being inspected.

23. A method of claim 22, wherein said transducers are operably disposed for contacting opposing surfaces of said container, material, or fluid or being inspected.

24. A method of claim 22, wherein said at least two transducers are in vertical and horizontal alignment to each other.

25. A method of claim 22, wherein said at least two transducers include a 1 MHz transducer and a 5 MHz transducer, with operational frequencies of 0 MHz to 2 MHz or of 0 MHz to 10 MHz, respectively.

26. A method of claim 22, wherein said excitation pulse(s) or waveform(s) is a wide-band, frequency-modulated, amplitude-modulated pulse or waveform.

27. A method of claim 22, wherein said excitation pulse(s) or waveform(s) is an encoded chirp.

28. A method of claim 27, wherein said encoding of said excitation pulse(s) or waveform(s) comprises pulse compression retaining frequency and amplitude information in received waveforms that permits deconvolution and cross-correlation of same.

29. A method of claim 27, wherein said excitation pulse(s) or waveform(s) comprises a linear frequency sweep with 90% of the pulse or waveform at full amplitude, wherein the excitation frequency extends from about 0 MHz to about 10 MHz.

30. A method of claim 22, wherein said excitation pulse(s) or waveform(s) is transmitted by a first of said at least two transducers in pitch-catch mode through said container, material, or fluid being inspected and said received pulse(s) or waveform(s) are received by at least a second of said at least two transducers in pulse-echo mode.

31. A method of claim 30, wherein said first of said at least two transducers is operable for receiving all $2 \cdot n$ (even) echo pulse(s) (where $n=1, 2, 3 \ldots$) and said second of said at least two transducers is operable for receiving said excitation pulse or waveform and all $1 \cdot n$ (odd) echo pulse(s) (where $n=3, 5, 7 \ldots$).

32. A method of claim 22, wherein said portion of said pulse(s) or waveform(s) is a gated portion selected from a cross correlation thereof of a selected frequency range.

33. A method of claim 32, wherein said analysis of said pulse(s) or waveform(s) comprises deconvolution and a fast Fourier transform of said gated portion(s).

34. A method of claim 22, wherein said analysis of said pulse(s) or waveform(s) comprises deconvolution by cross-correlation of same with said excitation pulse(s) or waveform(s) for determining acoustic wave speed as a first acoustic discrimination signature and relative attenuation coefficient as a second discrimination signature for identifying said material or said fluid.

35. A method of claim 22, wherein said first and second acoustic discrimination signatures are acoustic wave speed and relative acoustic attenuation, respectively.

36. A method of claim 22, wherein said analysis of said pulse(s) or waveform(s) includes correction for degree of curvature of a container surface.

37. A method of claim 22, wherein said analysis of said pulse(s) or waveform(s) includes correction for thickness of a container wall ascertained in conjunction with acoustic echoes and time-of-flight measurements.

38. A method of claim 22, wherein said analysis of said pulse(s) or waveform(s) includes correction for container composition selected from the group consisting of metal, plastic, ceramic, glass, or combinations thereof.

* * * * *